US012721584B2

(12) United States Patent
Ketcha et al.

(10) Patent No.: US 12,721,584 B2
(45) Date of Patent: Sep. 1, 2026

(54) SYSTEMS AND METHODS FOR IMAGING WIDE FILM RADIOGRAPHS

(71) Applicant: Medtronic Navigation, Inc., Louisville, CO (US)

(72) Inventors: Michael D. Ketcha, Brookline, MA (US); Patrick A. Helm, Canton, MA (US); Kyo C. Jin, Durham, NH (US)

(73) Assignee: Medtronic Navigation, Inc., Lafayette, CO (US)

( * ) Notice: Subject to any disclaimer, the term of this patent is extended or adjusted under 35 U.S.C. 154(b) by 142 days.

(21) Appl. No.: 18/608,592

(22) Filed: Mar. 18, 2024

(65) Prior Publication Data

US 2024/0358340 A1 Oct. 31, 2024

Related U.S. Application Data

(60) Provisional application No. 63/461,787, filed on Apr. 25, 2023.

(51) Int. Cl.

| | |
|---|---|
| ***A61B 6/00*** | (2024.01) |
| ***A61B 6/08*** | (2006.01) |
| ***A61B 6/40*** | (2024.01) |
| ***A61B 6/42*** | (2024.01) |
| ***A61B 6/58*** | (2024.01) |

(52) U.S. Cl.

CPC .................. *A61B 6/54* (2013.01); *A61B 6/08* (2013.01); *A61B 6/4028* (2013.01); *A61B 6/4233* (2013.01); *A61B 6/588* (2013.01)

(58) Field of Classification Search

None

See application file for complete search history.

(56) References Cited

U.S. PATENT DOCUMENTS

| | | | |
|---|---|---|---|
| 4,236,081 | A | 11/1980 | Klausz |
| 6,940,941 | B2 | 9/2005 | Gregerson et al. |
| 7,001,045 | B2 | 2/2006 | Gregerson et al. |
| 7,106,825 | B2 | 9/2006 | Gregerson et al. |
| 7,108,421 | B2 | 9/2006 | Gregerson et al. |
| 7,188,998 | B2 | 3/2007 | Gregerson et al. |
| 7,338,207 | B2 | 3/2008 | Gregerson et al. |
| 7,965,811 | B1 | 6/2011 | Gregerson et al. |
| 8,238,631 | B2 | 8/2012 | Hartmann et al. |
| 8,562,211 | B2 | 10/2013 | Helm et al. |
| 9,398,886 | B2 | 7/2016 | Gregerson et al. |
| 10,881,371 | B2 | 1/2021 | Helm et al. |

(Continued)

FOREIGN PATENT DOCUMENTS

| | | |
|---|---|---|
| EP | 1189537 B1 | 9/2004 |

OTHER PUBLICATIONS

International Search Report and Written Opinion for related International Application No. PCT/IB2024/054014; Date of Mailing: Jul. 22, 2024; 13 pages.

(Continued)

*Primary Examiner* — Marcus H Taningco

(74) *Attorney, Agent, or Firm* — Harrity & Harrity, LLP

(57) ABSTRACT

A method of operating an image apparatus and the imaging apparatus. The method operable to acquire image data of an object with a detector in a selected orientation. The method further operable to acquire image data at an effective detector larger than a physical detector. The image apparatus configured carry out the method.

20 Claims, 17 Drawing Sheets

(56) References Cited

U.S. PATENT DOCUMENTS

| | | | | |
|---|---|---|---|---|
| 11,138,768 | B2 | 10/2021 | Helm et al. | |
| 2010/0232565 | A1 | 9/2010 | Ye et al. | |
| 2014/0205074 | A1 | 7/2014 | Gregerson et al. | |
| 2019/0282185 | A1* | 9/2019 | Gregerson | A61B 6/4488 |
| 2020/0121267 | A1 | 4/2020 | Deutschmann | |
| 2020/0315553 | A1 | 10/2020 | Helm et al. | |
| 2021/0177365 | A1 | 6/2021 | Faulhaber et al. | |

OTHER PUBLICATIONS

Loop-X Mobile IMaging Robot, Brianlab AG, https://www.brainlab.com/surgery-products/overview-platform-products/robotic-intraoperative-mobile-cbct/, accessed Jun. 18, 2024.

* cited by examiner 92
16
91
40
13
200
11
33
56
52
$X_s$
C1
A1
L
54
15
$X_d$
58
94
14a
100

92
93
40
16
13
200
11
33
56
52
C1
A1
54
15
58
94
14b
100

92
40
16
95
13
200
11
33
56
52
57
$X_{s'}$
L
A1
C1
54
15
58
$X_{d'}$
94
14c
100

16
92
91
40
13
200
11
52
33
56
A1
54
15
58
94
14a
100

16
92
93
40
13
200
11
52
33
56
A1
54
15
58
94
14b
100

16
92
95
40
13
200
11
52
33
56
A1
54
15
58
94
14c
100

16
A1
200
40
91'
13
15
58
11
52
14a'
56
100
54
33

16
A1
11
52
200
15
58
40
93'
14b'
13
54
100
56
33

16
A1
11
52
56
200
15
100
95'
40
14c'
13
54
58
33

SYSTEMS AND METHODS FOR IMAGING WIDE FILM RADIOGRAPHS

CROSS-REFERENCE TO RELATED APPLICATION

This application claims the benefit of and priority to U.S. Provisional Patent Application No. 63/461,787 filed Apr. 25, 2023, the entire disclosure of which is incorporated by reference herein.

FIELD

The present disclosure relates to imaging a subject, and particularly to a system to acquire image data for generating a wide image, such as a wide film radiograph.

BACKGROUND

This section provides background information related to the present disclosure which is not necessarily prior art.

A subject, such as a human patient, may undergo a procedure. The procedure may include a surgical procedure to correct or augment an anatomy of the subject. The augmentation of the anatomy can include various procedures, such as movement or augmentation of bone, insertion of an implant (i.e. an implantable device), or other appropriate procedures.

A surgeon can perform the procedure on the subject with images of the subject that are based on projections of the subject. The images may be generated with image data generated with various imaging systems such as a magnetic resonance imaging (MRI) system, computed tomography (CT) system, fluoroscopy (e.g. C-Arm imaging systems), or other appropriate imaging systems.

SUMMARY

This section provides a general summary of the disclosure, and is not a comprehensive disclosure of its full scope or all of its features.

An imaging system may be used to acquire image data of the subject. The imaging system may generally include a source and a detector that are movable within an annular gantry. The source and detector may be positioned on a rotor such that they are able to move relative to one another. Further, the rotor may be able to rotate around a center of the annular gantry. During a coordinated or synchronized motion of the source, the detector, and the rotor a plurality of projections may be acquired that are substantially parallel or on a single plane with one another. The synchronized movement allows for an effective detector size to be greater than a size of the detector in the imaging system. The effective detector size may be as great as a diameter of the annular gantry and/or a dimension of a chord that is parallel to the diameter of the annular gantry.

At least one example embodiment relates to a method of operating an image apparatus. The method may include positioning a detector to image at least a portion of a volume configured to hold an object, utilizing a detector positioner to reposition the detector to multiple positions, such that a surface of the detector is parallel to a first axis, faces a first direction, and is configured to move to each of the multiple positions, and repositioning a beam source such that the beam source is at a position that is generally opposed to the detector, such that a center of a beam produced by the beam source is normal to a center of the surface of the detector when the surface of the detector is parallel to the first axis at all of the multiple positions. The first direction may be normal to the first axis. Repositioning the detector and repositioning the beam source may allow the center of a beam produced by the beam source to be maintained as normal to the center of the surface of the detector and the surface of the detector to be maintained as parallel to the first axis.

In at least one example embodiment, the method may further include rotating a rotor to allow repositioning of the detector and repositioning of the beam source.

In at least one example embodiment, the method may utilize a controller to control repositioning of the detector and repositioning of the beam source. The controller may be configured to reposition the detector and the beam source synchronously to achieve each of the multiple positions, particularly with the detector to form the effective detector dimension.

In at least one example embodiment, the method may further include rotating a rotor to allow repositioning of the detector and repositioning of the beam source synchronously with swiveling of the beam source and movement of the detector on the rails of the detector positioner.

In at least one example embodiment, the detector may be configured to move on rails of the detector positioner. The beam source may be configured to swivel. The detector may move on the rails of the detector positioner and the beam source may swivel to allow the center of a beam produced by the beam source to be maintained as normal to the center of the surface of the detector.

In at least one example embodiment, the method may further include imaging at least a portion of the volume at each of the multiple positions.

In at least one example embodiment, the method may further include at least one of determining a non-isocentric position using at least one image captured, determining a size of an object within the volume, determining a location and extent of truncation of an image and altering a subsequently prepared image based on the truncation, and determining a region of interest and determining a field of view, such that the region of interest is present in the field of view.

At least one example embodiment relates to an imaging apparatus. The apparatus may include a source that projects a radiation beam, a detector located a distance from the source and configured to receive the radiation beam, an imaging area between the source and the detector, the radiation beam from the source passing through a portion of the imaging area before it is received at the detector, a detector positioner configured to reposition the detector, a beam positioner configured to alter a trajectory of the radiation beam, a gantry housing the source, the detector, the detector positioner, and the beam positioner. A processor may be configured to direct the detector positioner to position the detector at a first position within the gantry to image a first portion of an object within the imaging area, direct the beam positioner to position the source such that the source is opposed to the detector at the first position and a beam produced by the source is detected by the detector at the first position, direct the detector positioner to move the detector to a second position within the gantry to image a second portion of the object within the imaging area, and direct the beam positioner to move the source such that the source is opposed to the detector at the second position and a beam produced by the source is detected by the detector at the second position. A surface of the detector may face a first direction in the first position. The surface of the detector may face the first direction in the second position.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Figure 5A:
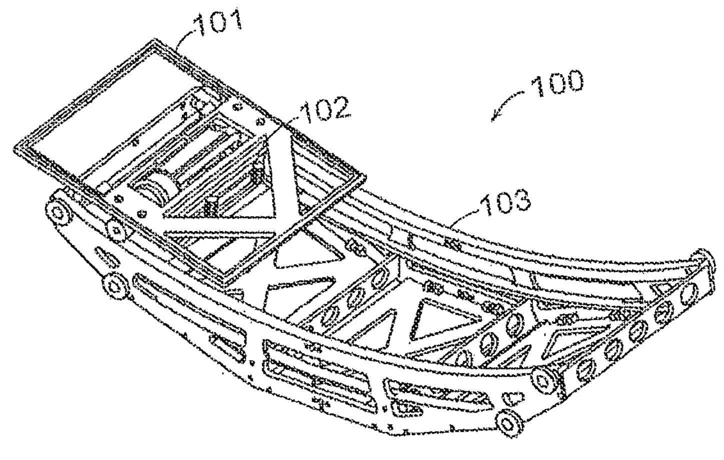
Figure 5B:
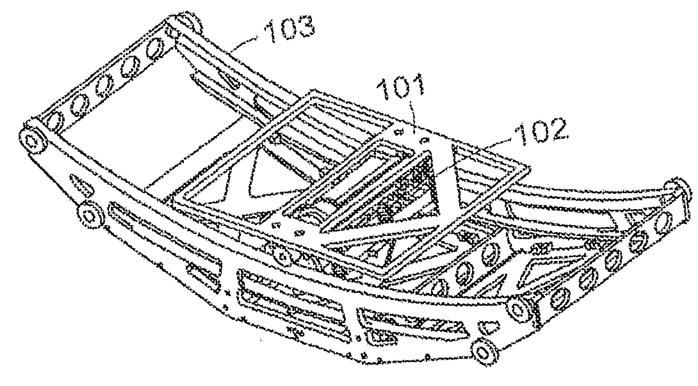
Figure 5C:
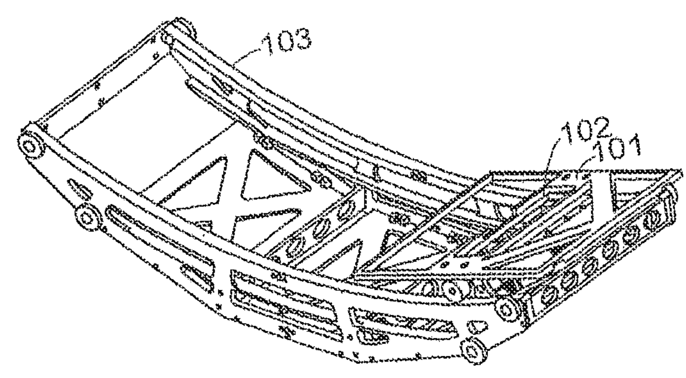
Figure 6:
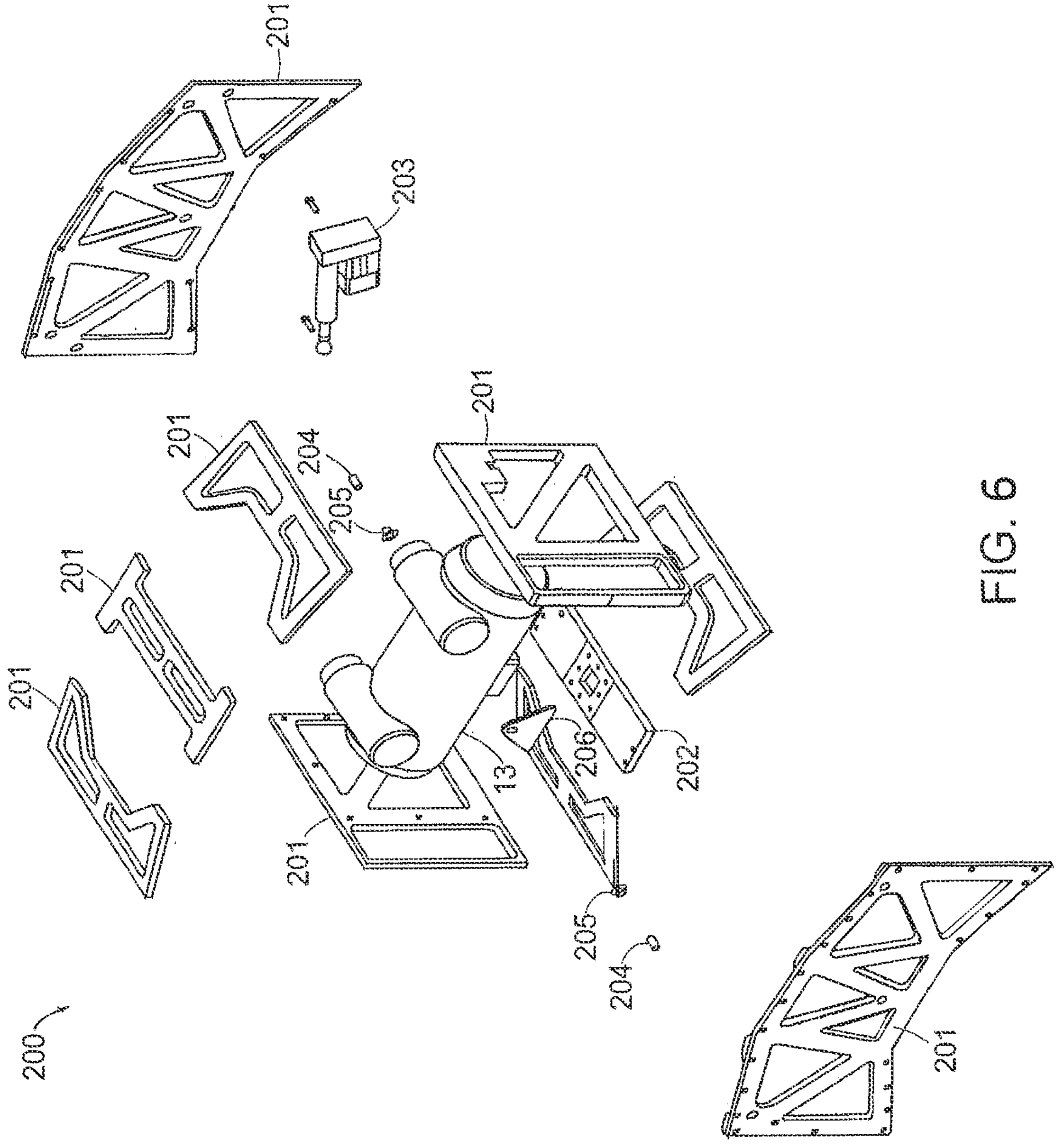
Figure 7:
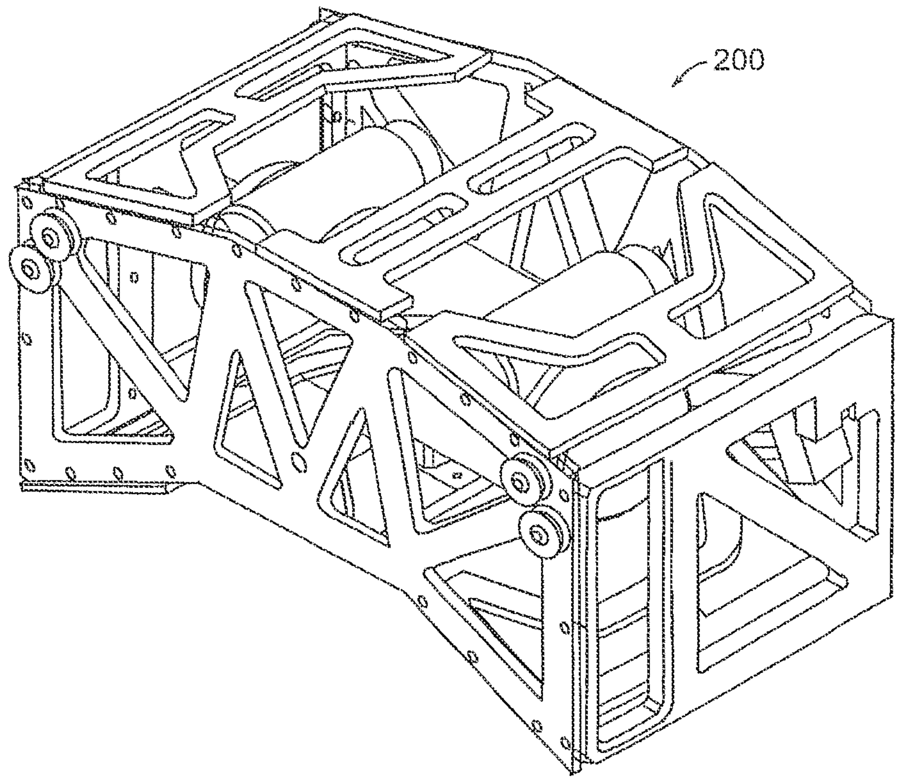
Figures 8A, 8B:
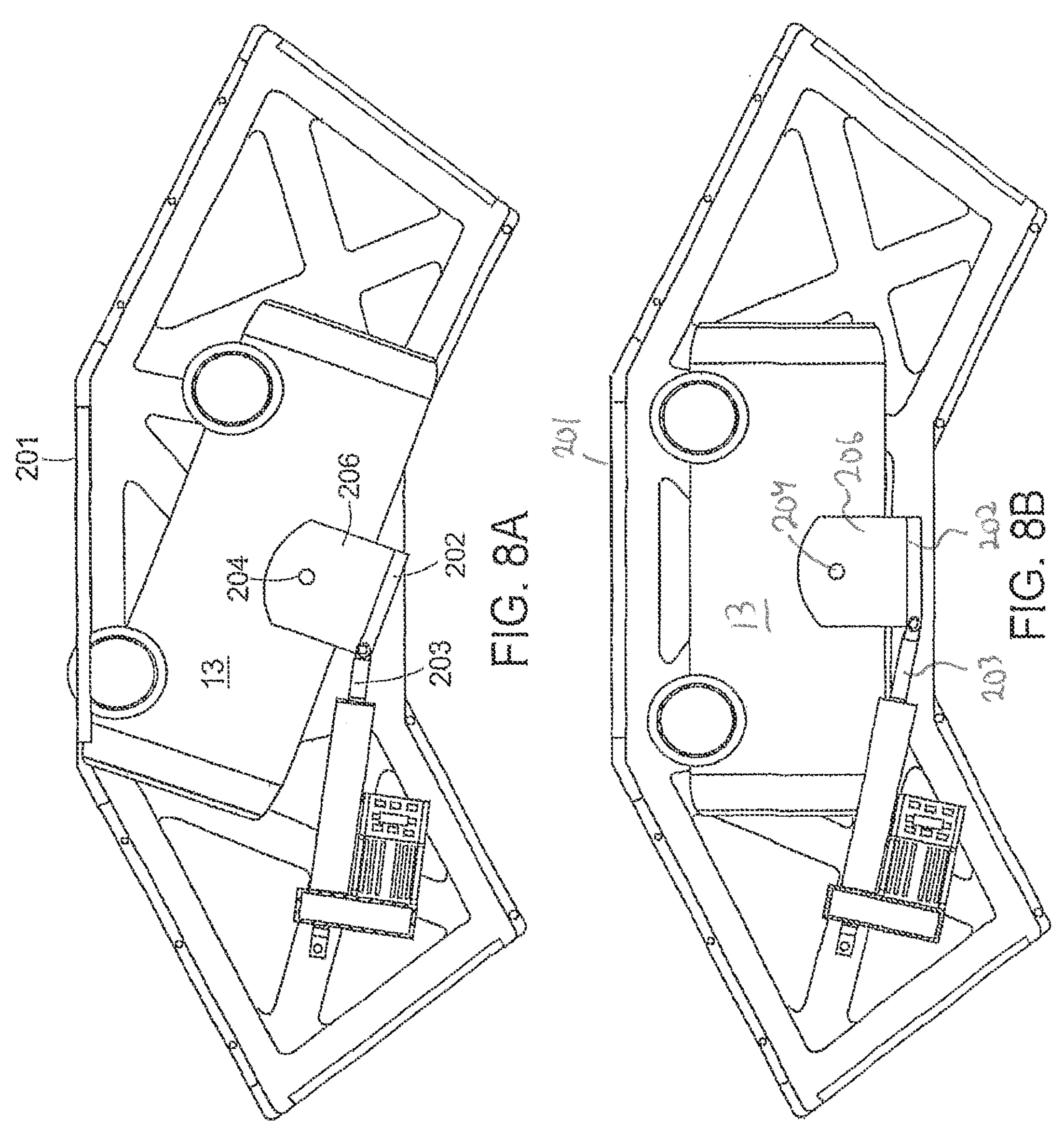
Figure 8C:
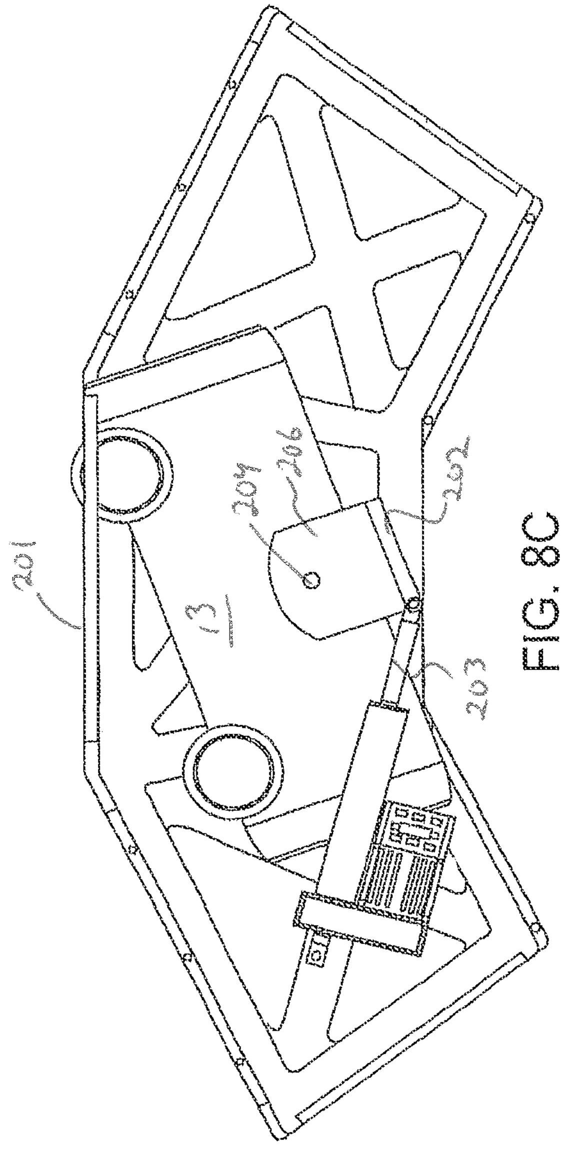
Figure 9:
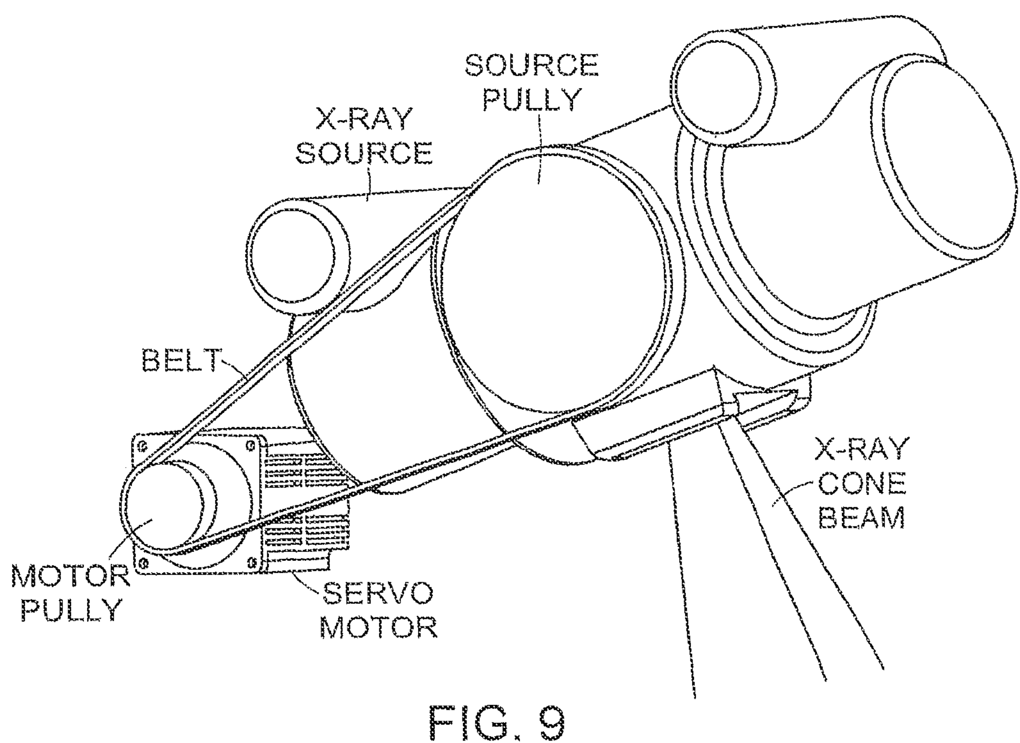
Figure 10:
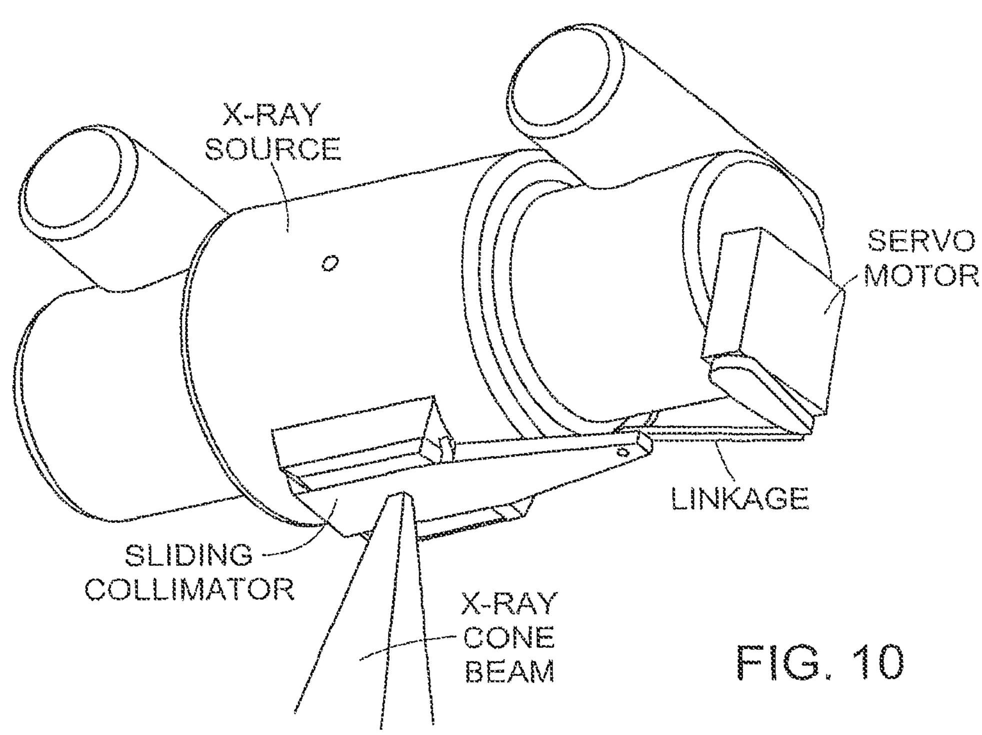
Figure 11:
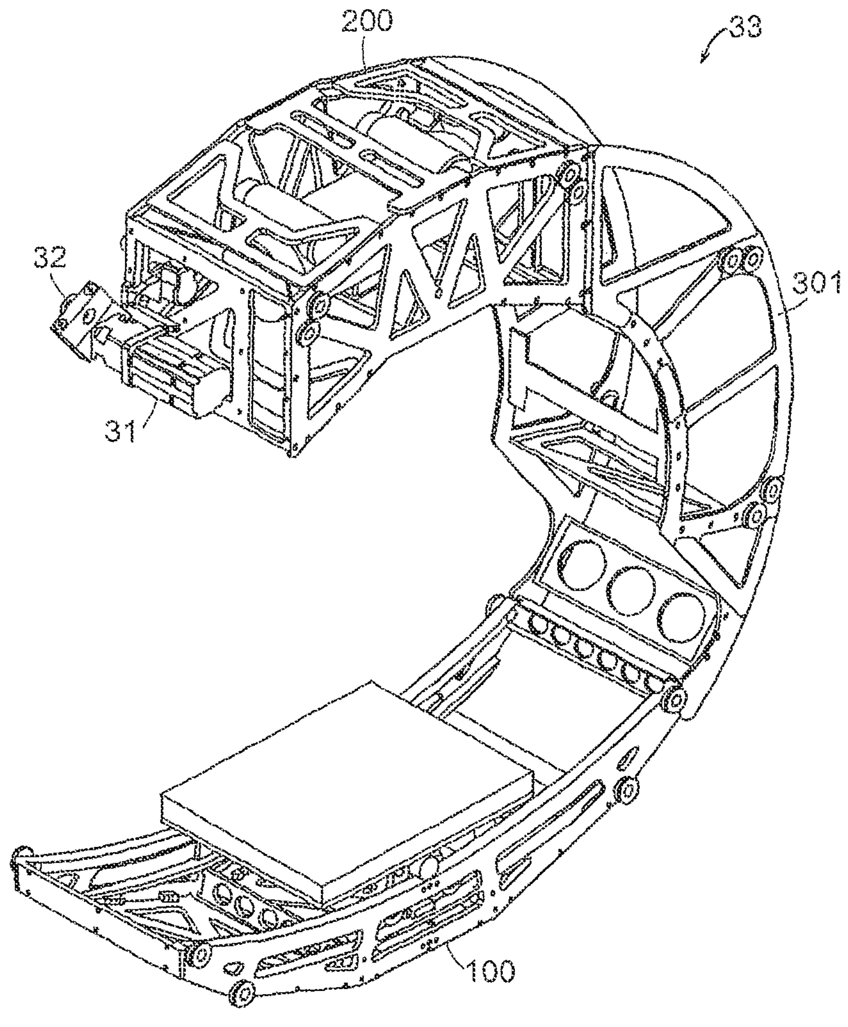
Figure 12:
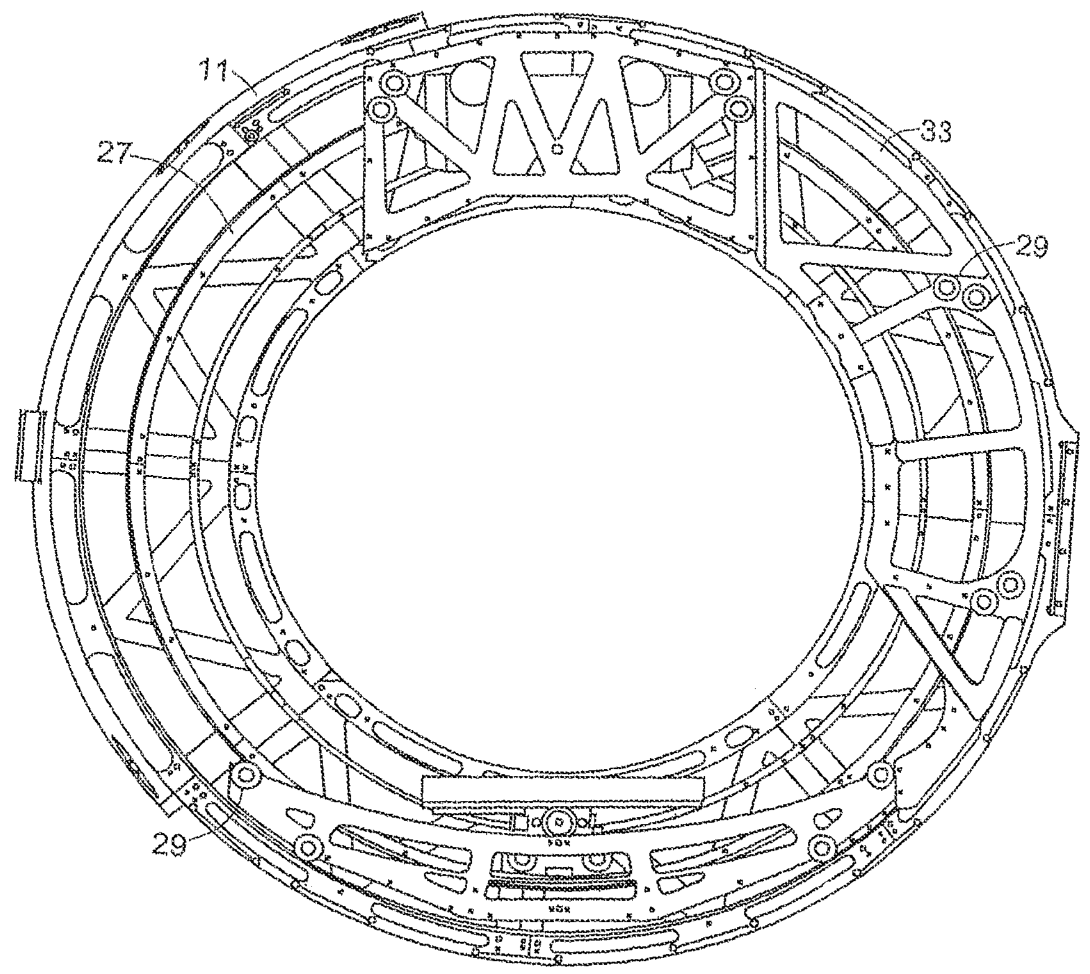
Figures 13A, 13B, 13C:
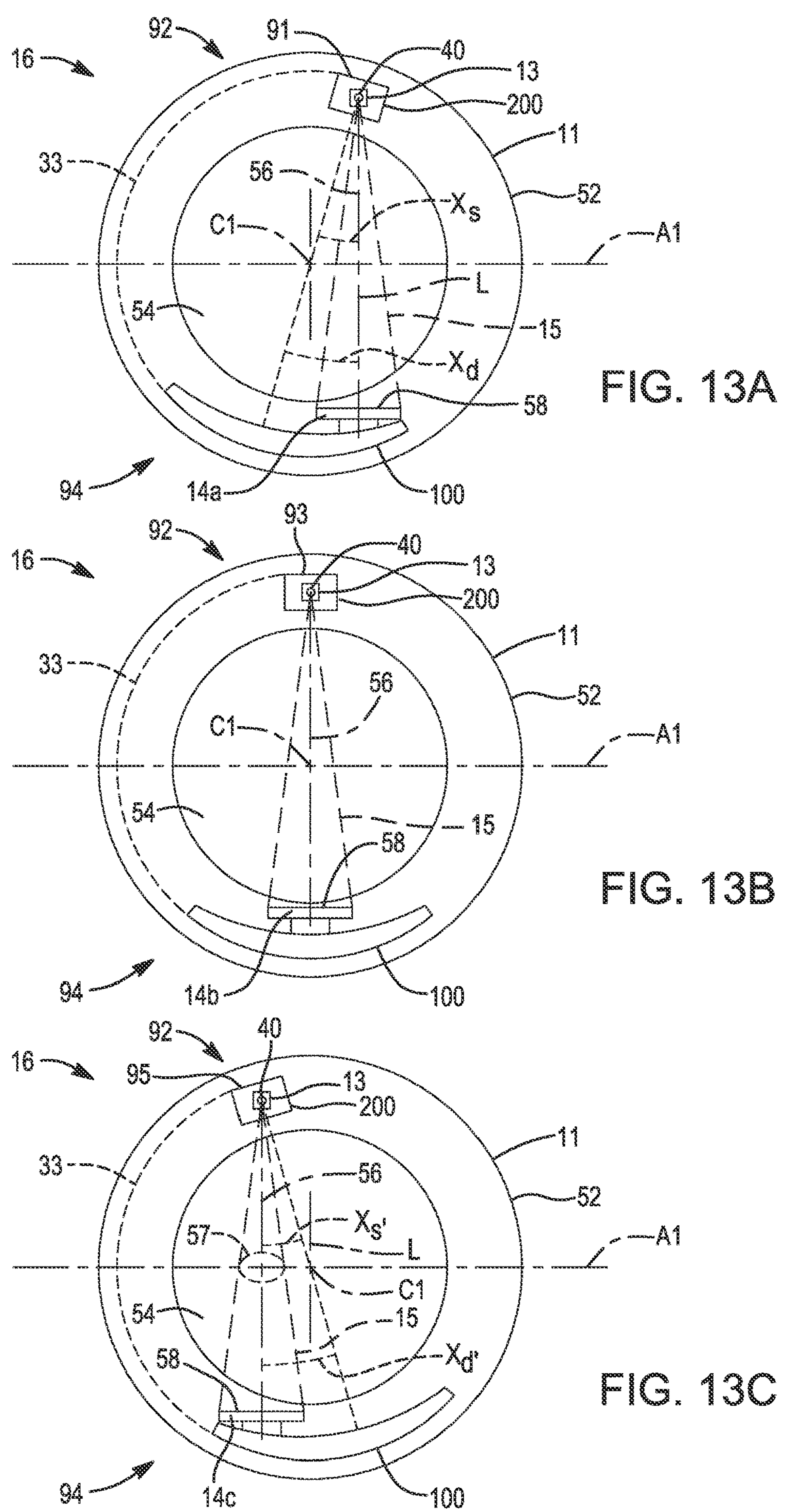
Figure 14:
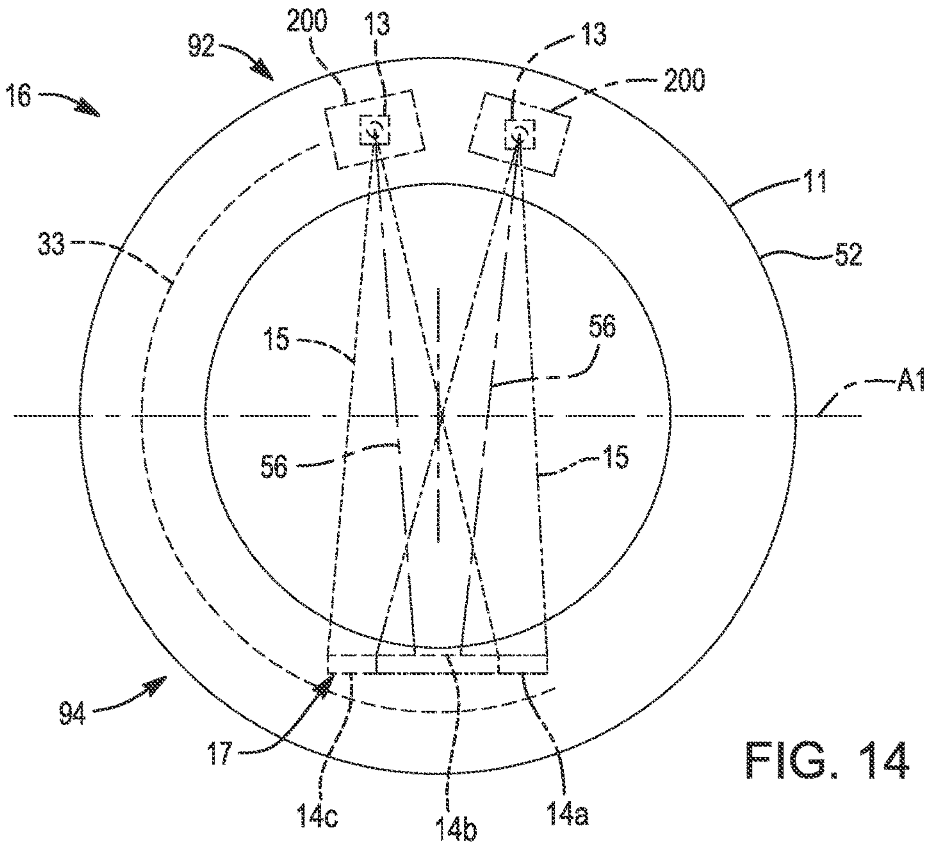
Figure 15:
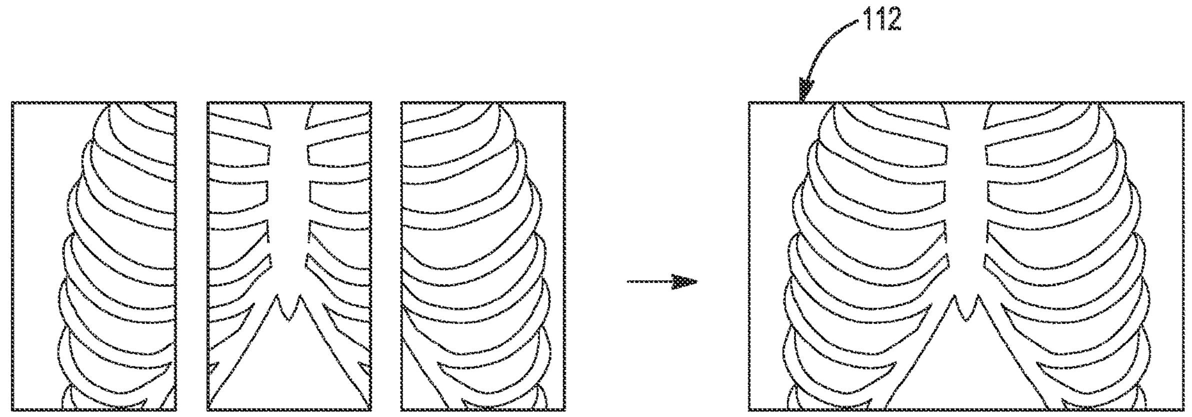
Figure 16:
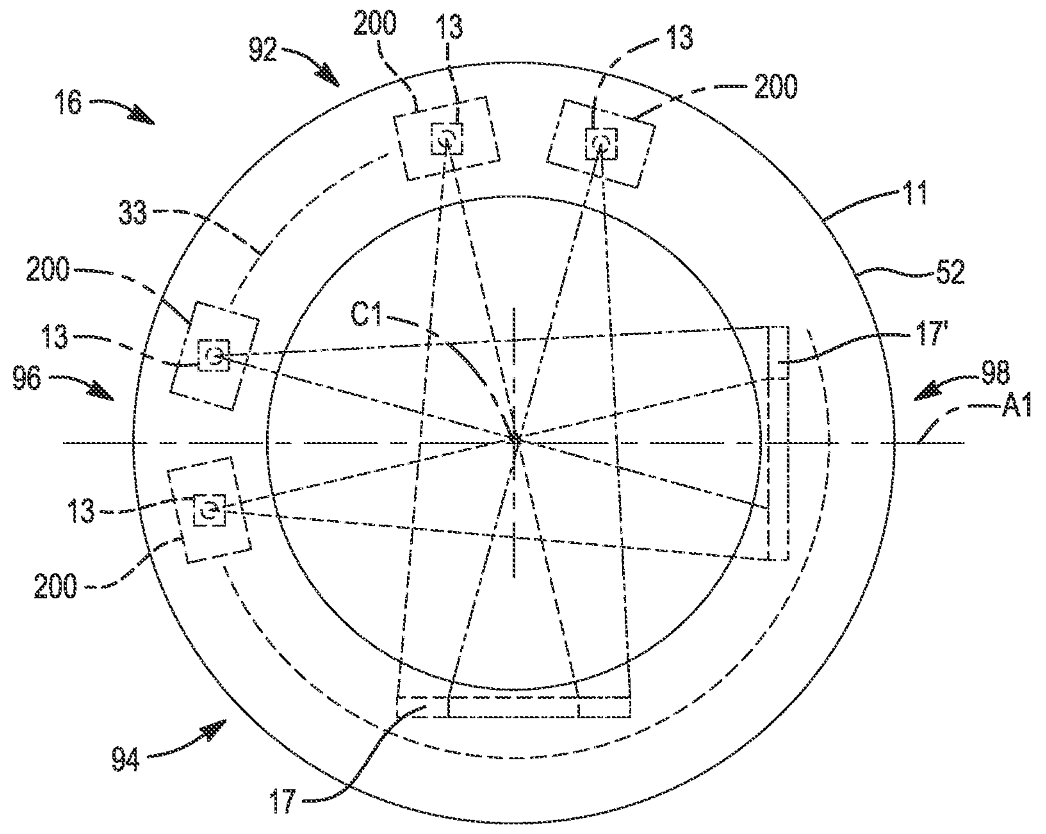

FIGS. 5A-C shows the x-ray detector positioned in three positions;

FIG. 6 is an exploded view of an x-ray source and source positioning stage according to one embodiment of the invention;

FIG. 7 is a perspective view of an assembled x-ray source and positioning stage;

FIGS. 8A-C shows an x-ray source tilted to three positions by a linear actuator, according to one embodiment of the invention;

FIG. 9 shows a motorized belt and pulley system for tilting an x-ray source to multiple positions, according to another embodiment;

FIG. 10 shows a motorized sliding collimator for directing an x-ray beam to multiple detector positions, according to yet another embodiment;

FIG. 11 is a perspective view of a rotor assembly for rotating an x-ray source and detector within a gantry;

FIG. 12 is a cutaway side view showing the rotor assembly within a gantry ring;

FIGS. 13A-C are schematic diagrams illustrating an x-ray source and a detector of an imaging system with a repositioning detector array according to one embodiment of the invention;

FIG. 14 illustrates the field-of view in a wide film radiograph achievable with the repositioning detector system;

FIG. 15 shows exemplary images stitched together to form a stitched image;

FIG. 16 illustrates the field-of-view achievable in multiple wide film radiographs from multiple views with the repositioning detector system; and FIGS. 17A-F are schematic diagrams illustrating an x-ray source and a detector of an imaging system with a repositioning detector array according to one embodiment of the invention.

Figure 18:
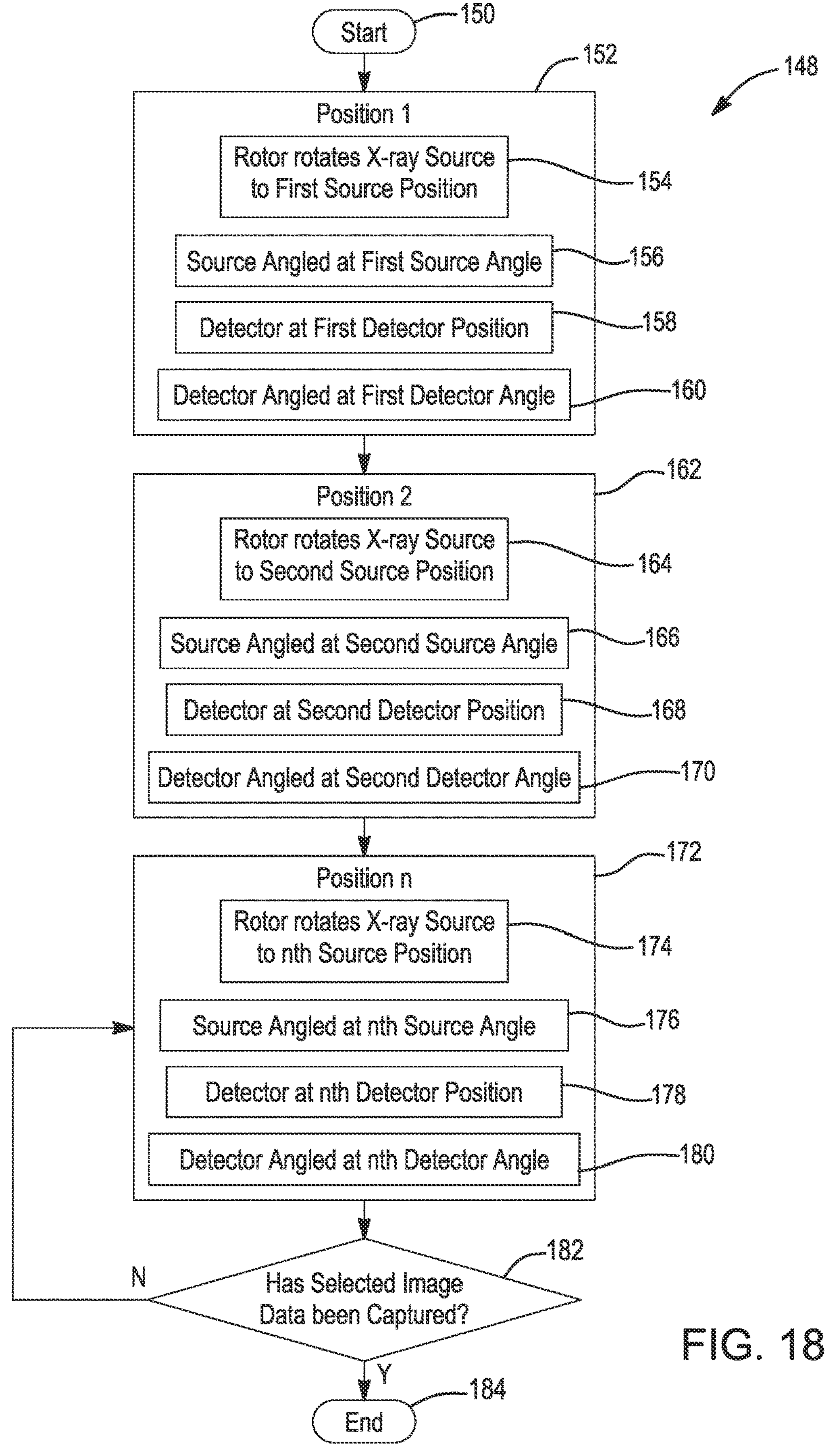

FIG. 18 is a flow chart of a method of operating the imaging system according to one embodiment of the invention.

Corresponding reference numerals indicate corresponding parts throughout the several views of the drawings.

DETAILED DESCRIPTION

Example embodiments will now be described more fully with reference to the accompanying drawings.

Imaging systems may be used for a variety of reasons, including providing images of patients in a medical setting. Imaging systems may provide acquire image data to generate multiple views of 2D and 3D images of such patients and/or any hardware. Commonly, imaging systems acquire image data relative to an isocenter of an imaging system. The isocenter is understood by one skilled in the art and generally includes essentially a center of an imaging system that is round or annular. However, the following disclosure provides an exemplary imaging system in which imaging need not include the isocenter of an imaging area. Such an imaging system allows imaging across an entire exemplary subject, in one example such imaging acquires image data from shoulder to shoulder of a patient. The imaging system includes an x-ray source, which projects a beam, onto a detector plate, such that the center of the beam is normal to a surface of the detector plate at a multitude of positions. In this manner, the detector motion remains parallel and generates a lateral shift of the imaging field.

Figure 1:
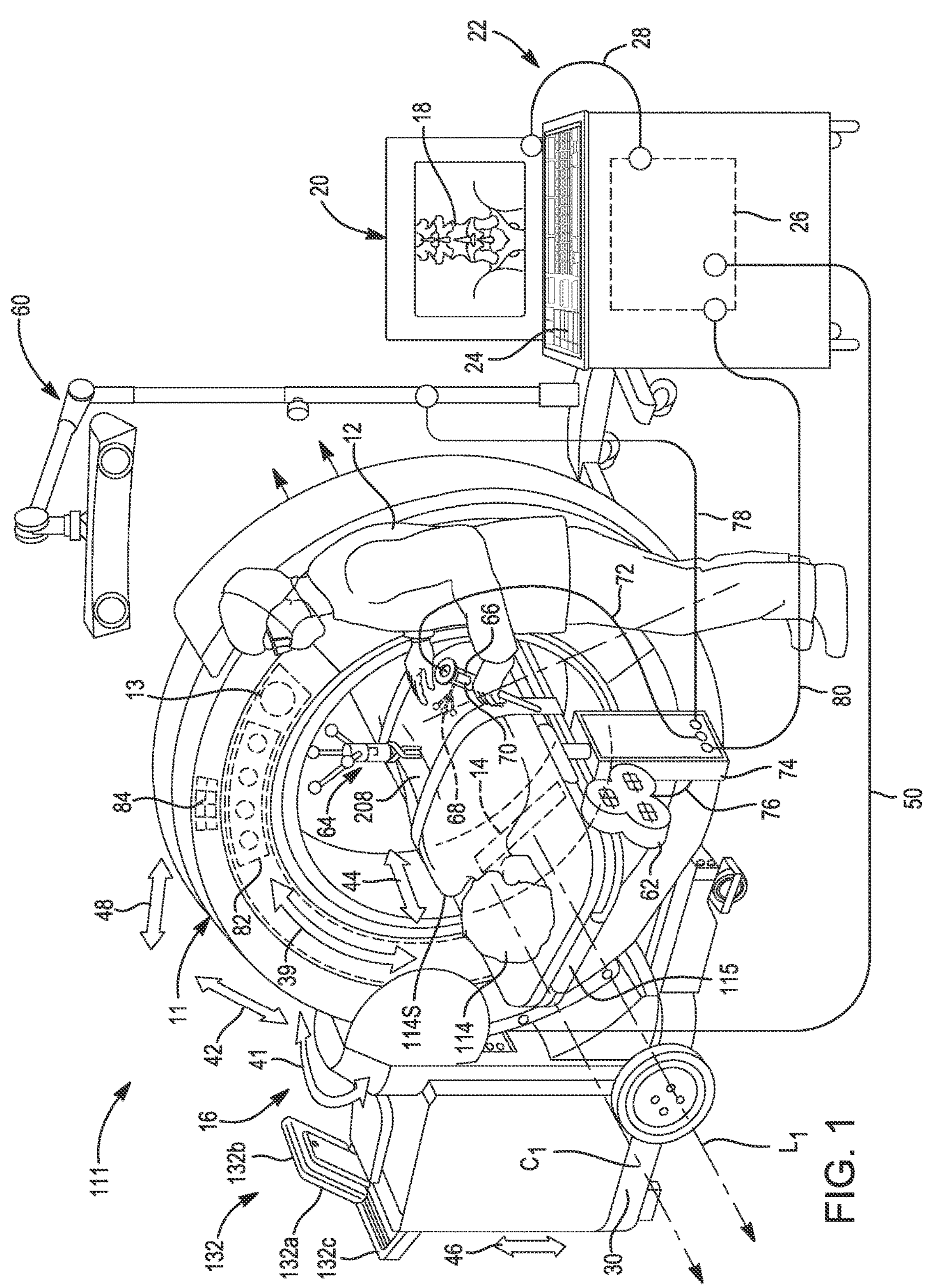
FIG. 1 is an environmental view of an exemplary imaging system in an operating theatre, with a source and a detector of the imaging system in a first position.

With reference to FIG. 1, in an operating theatre or operating room 111, a user, such as a user 12, can perform a procedure on a patient 114. In performing the procedure, the user 12 can use an imaging system 16 to acquire image data of the patient 114 for performing a procedure. The image data acquired of the patient 114 can include two-dimension (2D) projections acquired with an x-ray imaging system, including the system described herein.

In one example, a model can be generated using the acquired image data. The model can be a three-dimension (3D) volumetric model generated based on the acquired image data using various techniques, including algebraic iterative techniques. Displayed image data 18 can be displayed on a display device 20, and additionally, could be displayed on a display device 132*a* and associated with an imaging computing system 132, as will be discussed in greater detail herein. The displayed image data 18 can be a 2D image, a 3D image, or a time changing four-dimension image. The displayed image data 18 can include one or more of the types noted above.

It will be understood that the image data acquired of the patient 114 can be acquired as 2D projections, for example with an x-ray imaging system, as disclosed herein. The 2D projections can then be used to reconstruct the 3D volumetric image data of the patient 114. Also, theoretical or forward 2D projections can be generated from the 3D volumetric image data. Accordingly, it will be understood that image data can be either or both of 2D projections or 3D volumetric models.

The display device 20 can be part of a computing system 22. The computing system 22 can include a variety of computer-readable media. The computer-readable media can be any available media that can be accessed by the computing system 22 and can include both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the computing system 22. The computer-readable media may be accessed directly or through a network such as the Internet.

In one example, the computing system 22 can include an input device 24, such as a keyboard, and one or more processors 26 (the one or more processors can include multiple-processing core processors, microprocessors, etc.) that can be incorporated with the computing system 22. The input device 24 can comprise any suitable device to enable a user to interface with the computing system 22, such as a touchpad, touch pen, touch screen, keyboard, mouse, joystick, trackball, wireless mouse, audible control or a combination thereof. Furthermore, while the computing system 22 is described and illustrated herein as comprising the input device 24 discrete from the display device 20, the computing system 22 could comprise a touchpad or tablet computing device, and further, that the computing system 22 could be integrated within or be part of the imaging computing system 132 associated with the imaging system 16.

A connection 28 can be provided between the computing system 22 and the display device 20 for data communication to allow driving the display device 20 to illustrate the image data 18.

The imaging system 16 can include the O-Arm® imaging system sold by Medtronic Navigation, Inc. having a place of business in Louisville, Colo., USA. The imaging system 16, including the O-Arm® imaging system, or other appropriate imaging systems in use during a selected procedure are also described in U.S. Pat. No. 8,238,631, entitled "System And Method For Automatic Registration Between An Image And A Subject," filed on May 13, 2009, incorporated herein by reference. Additional description regarding the O-Arm imaging system or other appropriate imaging systems can be found in U.S. Pat. Nos. 8,562,211, 7,188,998, 7,108,421, 7,106,825, 7,001,045 and 6,940,941, each of which is incorporated herein by reference.

The O-Arm® imaging system 16 can include a mobile cart 30 that includes an imaging computing system 132 and an imaging gantry 11 in which is positioned a source 13 and a detector 14. With reference to FIG. 1, the mobile cart 30 can be moved from one operating theater or room to another and the gantry 11 can move relative to the mobile cart 30, as discussed further herein. This allows the imaging system 16 to be mobile so that it can be used in multiple locations and with multiple procedures without requiring a capital expenditure or space dedicated to a fixed imaging system.

Figure 2:
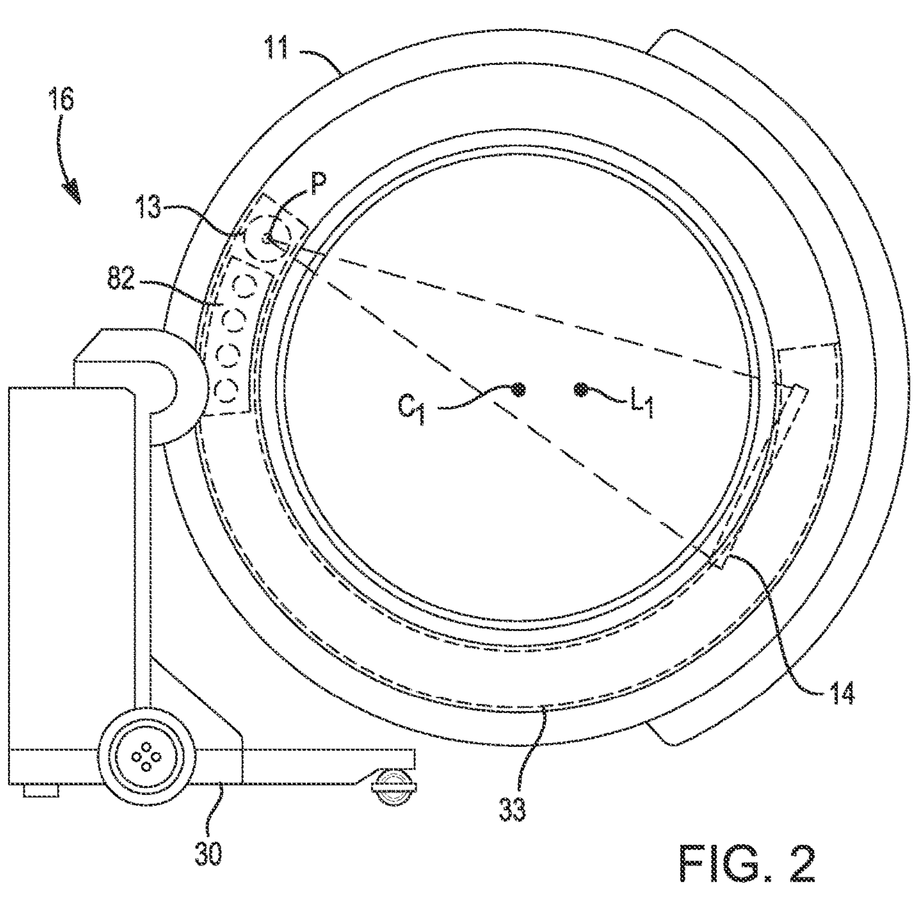
FIG. 2 is a schematic illustration of the imaging system of FIG. 1, with the source and the detector of the imaging system in a second position.

With reference to FIG. 2, the gantry 11 can define an isocenter of the imaging system 16. In this regard, a centerline C1 through the gantry 11 can pass through an isocenter or center defined by the imaging system 16, and any other line through the gantry 11, such as L1, can be considered to be off-isocenter or off-center of the imaging system 16. Generally, with reference to FIG. 1, the patient 114 can be positioned along the centerline C1 of the gantry 11, so that a longitudinal axis 114L of the patient 114 can be aligned with the isocenter of the imaging device 16. Image data acquired along the centerline C1 of the imaging device 16 can be considered isocenter or center image data, and image data acquired off-isocenter or off-center can be considered off-isocenter or off-center image data. Portions of the patient 114 may be off the isocenter and/or over the axis 114L, such as one or more of the shoulders 114*s* and/or portions of a thoracic region.

Generally, in the imaging gantry 11 the source 13 is opposed to the detector 14 across the isocenter of the imaging gantry 11 and may be connected to a rotor 33 which is configured to move within the imaging gantry 11. In other words, the source 13 may be on one side of the imaging gantry 11 and the detector 14 may be on a second or opposed side of the imaging gantry 11. In various embodiments, the rotor 33 may rotate at least 360 around inside the gantry 11. The source 13 and the detector 14 may also move relative to the rotor 33 and/or be fixed relative thereto.

Figure 3:
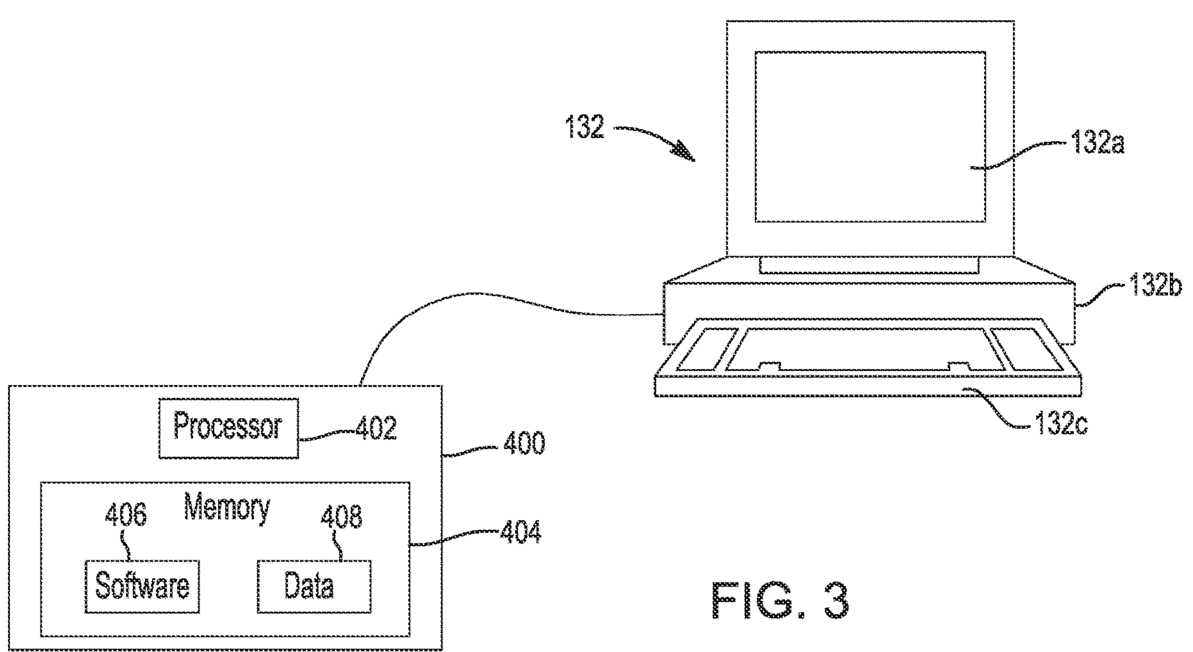
FIG. 3 is a schematic illustration of an exemplary computing system for use with the imaging system of FIG. 1.

With reference to FIG. 3, a diagram is provided that illustrates an exemplary embodiment of the imaging computing system 132, some or all of the components of which can be used in conjunction with the teachings of the present disclosure. The imaging computing system 132 can be incorporated into the computing system 22 and/or be separate therefrom. The imaging computing system 132 can include a variety of computer-readable media. The computer-readable media can be any available media that can be accessed by the imaging computing system 132 and includes both volatile and non-volatile media, and removable and non-removable media. By way of example, and not limitation, the computer-readable media can comprise computer storage media and communication media. Storage media includes, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which can be used to store computer-readable instructions, software, data structures, program modules, and other data and which can be accessed by the imaging computing system 132. The computer-readable media may be accessed directly or through a network such as the Internet.

In one example, the imaging computing system 132 comprises a display device 132*a* and a system unit 132*b*. As illustrated, the display device 132*a* can comprise a computer video screen or monitor. The imaging computing system 132 can also include at least one input device 132*c*. The system unit 132*b* includes, as shown in an exploded view at 400, a processor 402 and a memory 404, which can include software 406 and data 408.

In this example, the at least one input device 132*c* comprises a keyboard. It should be understood, however, that the at least one input device 132*c* can comprise any suitable device to enable a user to interface with the imaging computing system 132, such as a touchpad, touch pen, touch screen, keyboard, mouse, joystick, trackball, wireless mouse, audible control or a combination thereof. Furthermore, while the imaging computing system 132 is described and illustrated herein as comprising the system unit 132*b* with the display device 132*a*, the imaging computing system 132 could comprise a touchpad or tablet computing device or use display 20.

The imaging computing system 132 can control the movement, positioning and adjustment of the source 13, the detector 14 and rotor 33 independently to enable off-center image data acquisition via an off-center image control module, which can each be stored in the memory 404 and accessed by the processor 402. Thus, the off-center image control module may include a program of instructions to direct the imaging system 16 to move in a selected manner as discussed herein. A connection can be provided between the processor 402 and the display device 132*a* for data communication to allow driving the display device 132*a* to illustrate the image data 18.

With reference to FIG. 1, the gantry 11 can isometrically sway or swing (herein also referred to as iso-sway) generally in the direction of arrow 41, relative to the patient 114, which can be placed on a patient support or table 115. The gantry 11 can also tilt relative to the patient 114 illustrated by arrows 42, move longitudinally along the line 44 relative to the patient 114 and the mobile cart 30, can move up and down generally along the line 46 relative to the mobile cart 30 and transversely to the patient 114, and move perpendicularly generally in the direction of arrow 48 relative to the patient 114 to allow for positioning of the source 13/detector 14 relative to the patient 114. The rotor 33 may rotate generally in the direction of arrow 39.

The O-Arm® imaging system 16 can be precisely controlled by the imaging computing system 132 to move the source 13 and the detector 14 relative to the patient 114 to generate precise image data of the patient 114. In addition, the imaging system 16 can be connected with the processor 26 via connection 50 which can include a wired or wireless connection or physical media transfer from the imaging system 16 to the processor 26. Thus, image data collected with the imaging system 16 can also be transferred from the imaging computing system 132 to the computing system 22 for navigation, display, reconstruction, etc.

Briefly, with continued reference to FIG. 1, according to various embodiments, the imaging system 16 can be used with an unnavigated or navigated procedure. In a navigated procedure, a localizer, including either or both of an optical localizer 60 and an electromagnetic localizer 62 can be used to generate a field or receive or send a signal within a navigation domain relative to the patient 114. If desired, the components associated with performing a navigated procedure could be integrated within the imaging device 16. The navigated space or navigational domain relative to the patient 114 can be registered to the image data 18 to allow registration of a navigation space defined within the navigational domain and an image space defined by the image data 18. A patient tracker or a dynamic reference frame 64 can be connected to the patient 114 to allow for a dynamic registration and maintenance of registration of the patient 114 to the image data 18. The stitched images as described above may allow dynamic registration without the need for 3D image acquisition. Further information regarding registration and localization of image data was disclosed in previously filed U.S. Pat. No. 8,562,211 issued Oct. 22, 2013), which is incorporated herein by reference.

An instrument 66 can then be tracked relative to the patient 114 to allow for a navigated procedure. The instrument 66 can include an optical tracking device 68 and/or an electromagnetic tracking device 70 to allow for tracking of the instrument 66 with either or both of the optical localizer 60 or the electromagnetic localizer 62. The instrument 66 can include a communication line 72 with a navigation interface device 74, which can communicate with the electromagnetic localizer 62 and/or the optical localizer 60. Using the communication lines 72, 78 respectively, the navigation interface device 74 can then communicate with the processor 26 with a communication line 80. It will be understood that any of the connections or communication lines 28, 50, 76, 78, or 80 can be wired, wireless, physical media transmission or movement, or any other appropriate communication. Nevertheless, the appropriate communication systems can be provided with the respective localizers to allow for tracking of the instrument 66 relative to the patient 114 to allow for illustration of the tracked location of the instrument 66 relative to the image data 18 for performing a procedure.

It will be understood that the instrument 66 can be an interventional instrument and/or an implant. Implants can include a ventricular or vascular stent, a spinal implant, neurological stent or the like. The instrument 66 can be an interventional instrument such as a deep brain or neurological stimulator, an ablation device, or other appropriate instrument. Tracking the instrument 66 allows for viewing the location of the instrument 66 relative to the patient 114 with use of the registered image data 18 and without direct viewing of the instrument 66 within the patient 114. For example, the instrument 66 could be graphically illustrated as an icon superimposed on the image data 18.

Further, the imaging system 16 can include a tracking device, such as an optical tracking device 82 or an electromagnetic tracking device 84 to be tracked with a respective optical localizer 60 or the electromagnetic localizer 62. The tracking device 82, 84 can be associated directly with the source 13, the detector 14, rotor 33, the gantry 11, or other appropriate part of the imaging system 16 to determine the location or position of the source 13, detector 14, rotor 33 and/or gantry 11 relative to a selected reference frame. As illustrated, the tracking device 82, 84 can be positioned on the exterior of the housing of the gantry 11. Accordingly, the imaging system 16 can be tracked relative to the patient 114 as can the instrument 66 to allow for initial registration, automatic registration or continued registration of the patient 114 relative to the image data 18. Registration and navigated procedures are discussed in the above incorporated U.S. Pat. No. 8,238,631.

FIGS. 4-12 illustrate various details of hardware of the imaging system 16 according to an embodiment of the invention. The hardware, as discussed herein, may be uniquely moved and/or operated to achieve a selected imaging parameter. Some of hardware included in the imaging system 16 may be similar to that disclosed in U.S. Pat. No. 9,398,886, the entirety of which is incorporated herein by reference.

Figure 4:
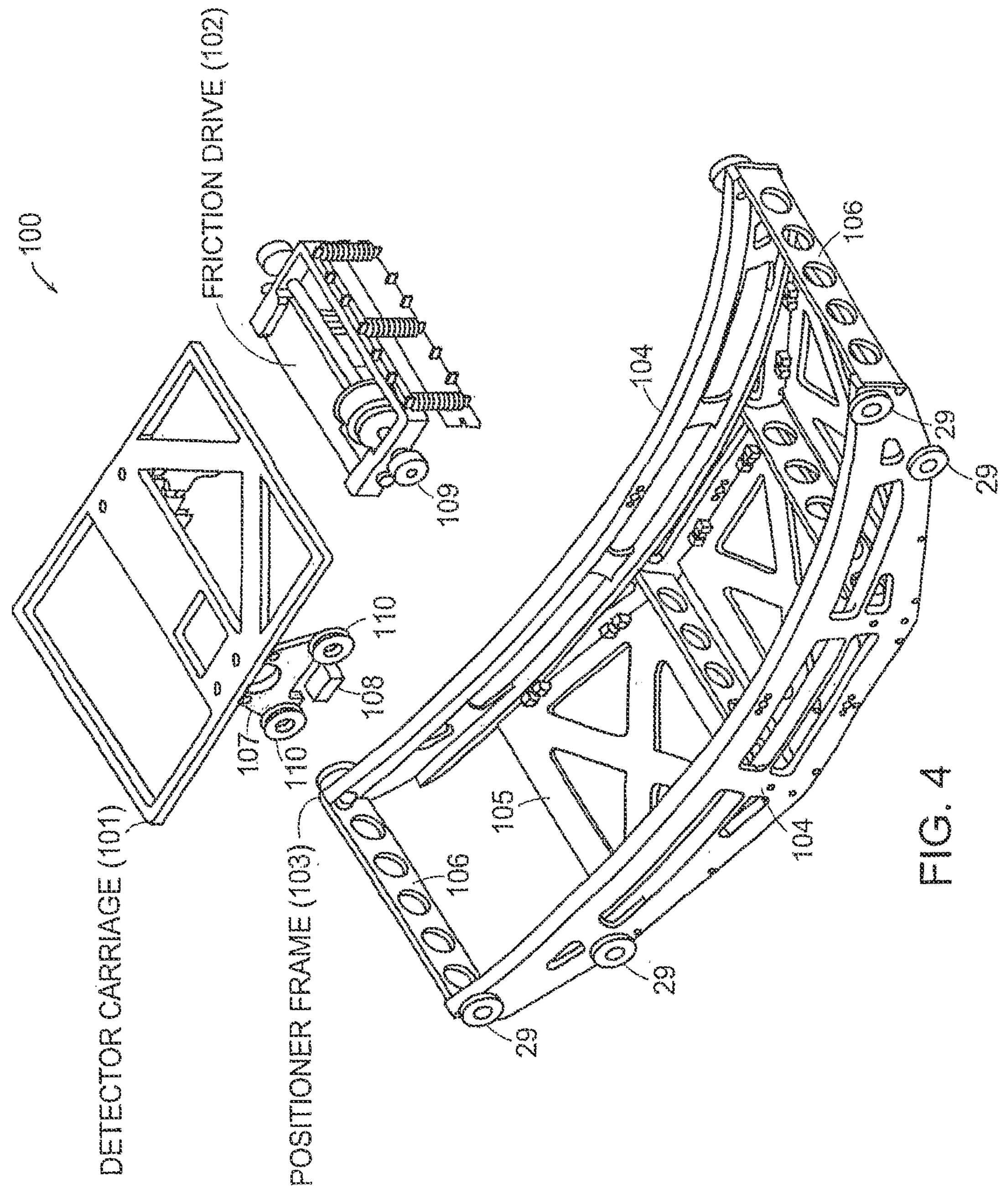
FIG. 4 is an exploded view of an x-ray detector positioning stage according to one embodiment.

Turning now to FIG. 4, an x-ray detector positioner 100 according to one embodiment of the invention is shown in exploded form. The detector positioner 100 comprises a detector carriage 101 for holding the detector, a drive 102 which attaches to the detector carriage, and a positioner frame 103 upon which the detector carriage is movably mounted. The positioner frame includes two parallel side walls 104, a base 105, and a series of lateral frames 106 extending between the side walls. The interior of the side walls 104 include three main concentric surfaces extending the length of the frame. On top of each side wall 104 is a flat surface upon which a friction wheel 109 is driven, in the center is a v-groove rail on which a pair of v-groove rollers 110 ride, and on the bottom is another flat surface upon which a linear encoder tape is affixed. The v-groove rails may be straight along a flat plane or line.

The drive 102 may include a servomotor, gear head, belt drive, axle, and friction wheels 109. The drive is mounted to the detector carriage 101 by brackets 107. The friction wheels 109 are preferably spring-loaded and biased against a flat top surface of the side walls 104. The rollers 110 are mounted to brackets 107, and pressed into the central v-grooves of the positioner side walls 104. The v-groove rollers 110 precisely locate the detector carriage 101 as well as allow loading from any direction, thus enabling the accurate positioning of the repositioning detector array independent of gantry angle or position. The friction wheel 109 can minimize and/or eliminate backlash in the positioning system. In addition, a read head 108 is located on a detector carriage bracket 107 for reading the encoder tape affixed to the bottom flat surface of the positioner side wall 104. The read head 108 provides position feedback information to the servomotor for precise positioning of the detector carriage along the v-groove rollers. The x-ray detector positioner 100 can also include bearings 29 attached to side walls 104 for rotating the entire detector assembly around the interior of a gantry, as described in further detail below.

Referring to FIGS. 5A-C, the assembled detector positioner 100 is shown repositioning the detector carriage 101 to multiple positions along the frame 103, which in various embodiments may be along an arc. The arc may be of any appropriate curve and may allow the detector 14 to be angled relative to the axis C1 and/or any axis parallel to C1. Also, a system arc is designed be angled relative to the beam source 13 which is an axis parallel to C1. The detector positioner 100 is shown repositioning the detector carriage 101 to multiple positions along an arc in FIGS. 5A-C. In operation, the detector carriage 101 and friction drive assembly 102 are precisely moved by the servomotor along the concentric axis of the positioning frame and accurately positioned by the linear encoder system. Three positions are shown in FIGS. 5A-C, although the detector carriage 101 may be precisely positioned at any point along the arc or line defined by the positioner frame 103. The compact nature of the friction drive 102 allows for maximum movement of the detector carriage 101 while the drive 102 remains completely enclosed within the positioner frame 103, and allows the distal ends of the detector carriage to extend beyond the edge of the positioner frame (as shown in FIGS. 5A and 5C) to further increase an “effective” field-of-view obtainable with the detector. In some embodiments, the detector carriage 101 may include an actuator, such as a motorized linear actuator, to allow a tilt of the detector 14. Such tilt of the detector 14 may allow the detector to translate along a line or remain parallel to an axis as the detector carriage 101 changes positions within the gantry 11.

As discussed above, the imaging system of the present invention preferably includes a radiation source with a beam positioning mechanism for changing the trajectory of the radiation emitted from a fixed focal spot, so that the beam may scan across multiple positions. One embodiment of an x-ray source stage 200 with a beam positioning mechanism is shown in FIG. 6. The stage comprises an outer wall frame 201 (shown in exploded form) which encloses the x-ray source 13, a swiveling x-ray source mount 202, and a servomotor linear actuator 203. The x-ray source 13 is supported on the bottom by source mount 202 and from the sides by a pair of bushing mounts 206. The bushing mounts 206 are connected to the outer wall frame 201 by precision dowel pins 204 that are press-fit into bushings 205. The dowel pins 204 permit the bushing mounts 206, and thus the x-ray source 13 and source mount 202, to pivot with respect to the outer wall frame 201 pivoting motion. This pivoting motion is preferably centered at the focal spot of the x-ray source.

The precision servomotor linear actuator 203 is attached at one end to the outer wall frame 201, and at the other end to the swiveling x-ray source mount 202. By varying the length of the motorized linear actuator 203, the source mount 202 and x-ray source 13 can be pivoted about dowel pins 204 to tilt the x-ray source about its focal spot in a controlled manner. The fully assembled x-ray source stage is shown in FIG. 7.

The operation of the x-ray source and tilting beam positioning mechanism is shown in FIGS. 8A-8C. As the linear actuator moves from a fully retracted position (FIG. 8A) to a fully extended position (FIG. 8C) the x-ray source pivots about its focal spot, thus altering the trajectory of the emitted radiation beam. In this embodiment, the pivot point represents the center of a circle with a radius defined by the distance from the focal spot to the center pixel of the detector array. The pivot angle is computed by determining the angle defined by the line connecting the focal spot of the x-ray detector and the center pixel of the detector array. A computerized motion control system can be used to synchronize the x-ray source tilt angle of the source 13 with the position of the detector 14 as it is repositioned so that the x-ray beam remains centered on the detector even as the detector repositions to different positions. In various embodiments, the computerized motion control system controls the x-ray source tilt angle such that the x-ray source moves alone a line or in a plane that remains substantially parallel to a line or plane of the detector as the detector translates along a line or flat plane.

Various other embodiments of an x-ray beam positioner can be employed. For example, as shown in FIG. 9, the x-ray source can be tilted to multiple positions by a motorized belt and pulley system. In another embodiment shown in FIG. 10, the trajectory of the x-ray beam is altered by a sliding collimator that is driven by a servomotor.

As shown in FIG. 11, the x-ray source stage 200 and x-ray detector positioner 100 can be joined together by a curved bracket assembly or rotor 301 to produce the C-shaped motorized rotor assembly 33. The rigid bracket 301 maintains the source and detector opposed to one another, and the entire rotor assembly 33 can be rotated inside an O-shaped x-ray gantry 11. The rotor assembly 33 can also include a motor 31 and drive wheel 32 attached at one end of the rotor 33 for driving the rotor assembly 33 around the interior of the gantry 11.

FIG. 12 is a cutaway side view of the gantry 11 which contains the C-shaped motorized rotor 33. The interior side walls of the gantry 11 include curved rails 27 extending in a continuous loop around the interior of the gantry 11. The drive wheel 32 of the rotor assembly 33 contacts the curved rail 27 of the gantry 11, and uses the rail 27 to drive the rotor assembly 33 around the interior of the gantry 11. A rotary incremental encoder can be used to precisely measure the angular position of the rotor assembly 33 within the gantry 11. The incremental encoder can be driven by a friction wheel that rolls on a concentric rail located within the sidewall of the gantry 11. The rotor assembly 33 also includes bearings 29, which mate with the curved rails 27 of the gantry 11 to help guide the rotor assembly 33 as it rotates inside the gantry 11. The interior of the gantry ring 11 can include a slip ring that maintains electrical contact with the rotor assembly 33 to provide the power needed to operate the x-ray source 13, detector 14, detector positioner 100, and/or beam positioner, and also to rotate the entire assembly within the gantry frame. The slip ring can furthermore be used to transmit control signals to the rotor, and x-ray imaging data from the detector to a separate processing unit located outside the gantry. Any or all of the functions of the slip ring could be performed by other means, such as a flexible cable harness attached to the rotor, for example.

Although the rotor assembly 33 illustrated in FIG. 11 is a C-shaped rotor, it will be understood that other rotor configurations, such as O-shaped rotors, could also be employed. For example, a second curved bracket 301 could be attached to close the open end of the rotor, and provide a generally O-shaped rotor. In addition, the x-ray source and detector may rotate independently of one another using separate mechanized systems.

The imaging system 16, according to various embodiments, includes the gantry 11 secured to a support structure, which could be a mobile or stationary cart, a patient table, a wall, a floor, or a ceiling. As shown in FIG. 1, the gantry 11 may be secured to the mobile cart 30 in a cantilevered fashion. In certain embodiments, the gantry 11 is configured to translate and/or rotate with respect to the support structure, including, for example, translational movement along at least one of the x-, y-, and z-axes, and/or rotation around at least one of the x- and y-axes. X-ray scanning devices with a cantilevered, multiple-degree-of-freedom movable gantry are described in U.S. Pat. No. 7,001,045, issued Feb. 21, 2006, and U.S. Pat. No. 7,338,207, issued Mar. 4, 2008, the entire teachings of which are incorporated herein by reference.

The O-shaped gantry can include a segment that at least partially detaches from the gantry ring 11 to provide an opening or "break" in the gantry ring 11 through which the object to be imaged may enter and exit the central imaging area 54 of the gantry ring 11 in a radial direction. An advantage of this type of device is the ability to manipulate the x-ray gantry 11 around the target object, such as a patient, and then close the gantry 11 around the object, causing minimal disruption to the object, in order to perform x-ray imaging. Examples of "breakable" gantry devices for x-ray imaging are described in U.S. Pat. No. 6,940,941, issued Sep. 6, 2005, incorporated herein by reference.

FIGS. 13A-C schematically illustrate an x-ray scanning system 16 with a repositioning detector array according to one embodiment of the invention. The scanning system 16 shown in FIGS. 13A-C includes gantry 11, which in this embodiment comprises a generally annular, or "O-shaped," housing 52 having a central opening 54 into which a subject (e.g., an object or a patient) being imaged is placed. The gantry 11 contains the x-ray source 13 (such as a rotating anode pulsed x-ray source) that projects a beam of x-ray radiation 15 into the central opening 54 of the gantry 11, through the object being imaged, and onto the detector 14 (such as a flat panel digital detector array) located on the opposite side of the gantry 11. The x-rays received at the detector 14 can then be used to produce a 2D planar or 3D tomographic object reconstruction images using well-known techniques.

The detector 14 may be repositioned to multiple positions. The multiple positions of the detector may, as discussed herein, allow a selected point on the detector 14 to move along a line or an arcuate path. In each of the positions in which the detector 14 is along the path, a substantially planar surface 58 of the detector 14 may be generally parallel to a first axis A1 (which may also be illustrated as a chord of the gantry 11), such that the line and/or first axis A1 are generally normal to a centerline 56 of a trajectory of beam 15 that passed through the isocenter or center C1 of the imaging system 16. In other words, when the detector 14 has the substantially planar surface 58, the surface 58 of the detector 14 will generally remain in a single plane during a selected image acquisition procedure. This permits the detector 14 to capture image data or projections (which may also be referred to as images that may be reconstructed from the image data) of selected portions of subjects within the gantry 11, including images of objects which are non-isocentric or not at an isocenter with the gantry 11. FIGS. 13A-C show schematic diagrams of the imaging area within the gantry 11, the source 13, and the detector 14. Illustrated in FIGS. 13A-C are exemplary three positions of the detector 14 as the detector 14 moves to three different positions which are parallel to the first axis A1 while the detector is generally opposed to the x-ray source 13 such that the detector 14 is operable to detect x-rays emitted by the source 13. It is understood, however, that the detector 14 may move to more or less than three positions. For example, FIG. 14 is a side view showing a resultant effective large imaging field-of-view detector 17 that may be formed by combining data obtained at all three source 13 and detector 14 positions 14*a*, 14*b*, and 14*c* shown in FIGS. 13A-C. The detector 14, however, need not be in only the three noted positions. The detector 14 may move continuously in a range of motion between the three noted positions, as discussed further herein.

The combination of positions and the resultant images from FIGS. 13A-C provides a large or wide "effective" detector 17 having a large or wide field-of-view, as shown in FIG. 14. A stitched image 112 may be obtained by combining three images together, resulting in a large field-of-view image using only the single detector 14 having a relatively small size, such as the stitched image shown in FIG. 15. The wide effective detector 17 represents the imaging area that is within a field-of-view that may be made by repositing the detector 14. Each of the images captured throughout the movement of the detector 14, may be stitched together using generally known techniques such as image blending, registration, and view manipulations. These may include blending various portions of images that are near matches (e.g. determined to be similar portions) to achieve continuity. for example, segmentation may occur in each of the images and matching portions may be identified and then used to align the different projections at each of the positions of the detector 14. A description of the construction of the stitched image 112 comprising the captured images is disclosed in U.S. Pat. No. 10,881,371, the entirety of which is incorporated herein by reference.

Additionally, stitched images may assist a care provider in selecting a region of interest for additional imaging. Appropriate detector shifts can then be determined based on the position of the region of interest. Alternatively, the source 13 and detector 14 may be positioned to center a single-shot image on an anatomical content of interest that is off the isocenter. For example, the single-shot (i.e., individual) images taken may provide a preferred view of the object. Once the single-shot views have been selected, the motion profiles (i.e., angles and locations of the various portions of the system 16) corresponding to the single-shot views can be used as the new image center for further non-isocentric scans. In other words, while a single wide field of view image may be stitched together including off isocenter projections, images may include only the off isocenter image data.

The stitched image 112 may be used to determine the size of the patient and extent of non-anatomical objects. This functionality may assist in determining an optimal dose of radiation for additional imaging, to assist in avoiding application of radiation. Such information can also be used to inform future image data acquisition for image reconstruction by compensating for image truncation, such as when an object is not completely shown in an image, but a larger image may provide a clearer image of the object. In other words, the stitched images 112 may assist in estimating the presence and extent of image truncation. This may also assist in identifying objects that may be truncated in smaller field of view images. For example, the stitched image may include an interfering object (e.g., a metallic object) that may distort an image. A small field of view image may not include any of the distorting object, but may be distorted thereby. The stitched image may be used to identify the distorting object and allow for compensation in a smaller field of view image by identifying its position relative to the smaller field of view.

The source 13 includes a beam positioning mechanism for changing the trajectory of the beam 15 from a stationary focal spot 40, so that the beam follows the detector as the detector 14 moves, as shown in FIGS. 13A-C, which is explained in further detail below. This permits safer and more efficient dose utilization, as generally only the region of the target object that is within the field-of-view of the detector 14 at any given time will be exposed to a radiation dose.

In one aspect, the x-ray source 13 (via the x-ray source stage 200) and repositionable detector 14 are rotatable around the interior of the gantry 11, such as on the motorized rotor 33. The rotor 33 may allow a rotation which may create a stitched image in at least one direction, such as the stitched image 112 shown in FIG. 15. The rotation provided by the rotor 33 will rotate the source stage 200 (and the source 13 therein) and the detector positioner 100 along the arcuate path of the rotor 33. As the rotor 33 rotates, the source stage 200 will maintain the same orientation relative to the rotor 33, which will cause the source 13 and the beam 15 generated thereby to face different directions relative to the isocenter C1 as the rotor 33 rotates when the source 13 is not angled relative to the source stage 200. Similarly, the detector positioner 100 will rotate with the rotor 33, such that the detector positioner 100 will face different directions relative to the isocenter C1 throughout the rotation.

In order to gather image data to create the stitched image 112, the source 13 begins in a first position 91 on a first side 92 of the gantry 11, which may also be referred to as a first region 92. The detector 14 at a first detector position 14*a* located on a second side 94 of the gantry, which may also be referred to as a second region 94 of the gantry 11, opposite and across the central opening 54 from the first side 92. The detector 14 is positioned in the first position 14*a* across the central opening 54 from the source 13 in the first position 91. In the example shown in FIG. 13A, when the source 13 and the detector 14 are placed in the first positions 91, 14*a*, both the source 13 and the detector 14 are on a single side (illustrated to the right) of isocenter C1. The beam positioning mechanism for changing the trajectory of the beam 15 may direct the beam 15 in a direction of the detector 14. For example, in FIG. 13A, the source 13 may be rotated an angle Xs by about zero (0) to about 13 degrees, including to about 9 degrees relative to the isocenter C1, which also rotates it relative to the source stage 200 such that the beam 15 is projected in the direction of the detector 14. When in the first position 14*a* shown in FIG. 13A, the detector 14 may be positioned near an end of the detector positioner 100. This angle may also be reflected on a second side of a line L that is perpendicular to the axis A1 at the isocenter C1. In order for the surface 58 of the detector 14 to be parallel with the first axis A1 in the first position, the detector 14 may rotate relative to the detector positioner 100 and/or be positioned at an angle relative to the rotor 33 such as via the arcuate frame rails. For example, in the first position shown in FIG. 13A, the detector 14 may be rotated an angle Xd which may be about 0 degrees to about 13 degrees, including about 9 degrees from the detector positioner in order to maintain a parallel position of the surface 58 relative to the first axis A1. This angle may also be reflected on a second side of a line L that is perpendicular to the axis A1 at the isocenter C1. Further, the angle Xd may be relative to the isocenter and the center of the source 13. An image may be captured when the source 13 and the detector 14 are in the respective first positions 91, 14*a* shown in FIG. 13A.

The rotor 33 may then rotate such that the x-ray source stage 200 is rotated such that the source 13 may be posited at a second position 93 located on the first side 92 of the gantry, which for example, may be in a center portion of the first side 92 as shown in FIG. 13B. As the rotor 33 rotates the x-ray source stage 200 to the second position (i.e., in a counter-clockwise direction), the x-ray source stage 200 may be angled such that a side of the source stage 200 is parallel with the first axis A1 when in the second position. In such a position, the beam positioning mechanism may place the source 13 at an angle such that the beam 15 is projected normal to the first axis A1 and the detector 14 when in the second position 14*b*, such as in FIG. 13B. As the rotor 33 rotates the detector positioner 100 to a second position (i.e., in a counter-clockwise direction), the detector positioner 100 is placed further right of isocenter C1, as illustrated in FIG. 13B when compared to the first position of FIG. 13A. In order to counteract this movement of the detector positioner 100, the detector 14 moves along the detector positioner 100 in a direction opposite the rotation of the rotor 33. For example, when going from the first position of FIG. 13A to the second position 14*b* as illustrated in FIG. 13B, the detector 14 moves in a direction opposite the movement of the rotor 33 and of the detector positioner 100. In order for the surface 58 of the detector 14 to remain parallel with the first axis A1 in the second position, the detector 14 may rotate relative to the detector positioner 100 and/or move along the arcuate path of the detector positioner 100. For example, in the second position 14*b* of the detector 14 shown in FIG. 13B, the detector 14 may be rotated and/or tilted about 0 degrees from the detector positioner in order to maintain a parallel position of the surface 58 relative to the first axis A1.

The movements of all of the portions, such as the source 13, the detector 14, and the rotor 33 may by synchronous such that the beam 15 follows the detector 14 as the components described above move from the first position 91, 14*a* to the second position 93, 14*b*. The motion profile for transitioning to the second position 93, 14*b* may comprise a rotation of the rotor 33 synchronized with a selected, which may be an equal and opposite, tilt of the source 13 and the detector 14. An image may be captured when the source 13 and the detector 14 are in the respective second positions.

The source 13 and the detector 14 may move to a third position 95, 14*c* in this manner, such as in FIG. 13C, and another projection may be captured. As the rotor 33 rotates the x-ray source stage 200 and the source 13 to the third position 95 (i.e., in a counter-clockwise direction), the x-ray source 13 may be titled relative to the first axis A1. In such a position, the beam positioning mechanism may rotate the source 13 by an angle Xs' may be the same magnitude, as discussed above (e.g., 9 degrees or negative 9 degrees relative to the line L) relative to the isocenter C1 and also angle relative to the source stage 200 such that the beam 15 is projected in the direction of the detector 14. The direction is generally opposite that of the direction as illustrated in FIG. 13A. As the rotor 33 rotates the detector positioner 100 and the detector 14 to the third position 14*c* (i.e., in a counter-clockwise direction), the detector positioner 100 may be placed further right of isocenter in FIG. 13C when compared to the second position of FIG. 13B. In order to counteract this movement of the detector positioner 100, the detector 14 moves along the detector positioner 100 in a direction opposite the rotation of the rotor 33. For example, when going from the second position 14*c* illustrated in FIG. 13B to the third position 14*c* illustrated in FIG. 13C, the detector 14 moves toward an end opposite the end of the first position 14*a* of the detector positioner 100. In order for the surface 58 of the detector 14 to be parallel with the first axis A1 in the third position, the detector 14 may rotate relative to the detector positioner 100 and/or move along an arcuate path of the position 100. For example, in the third position 14*c* shown in FIG. 13C, the detector 14 may be rotated an angle Xd' may be the same magnitude, as discussed above (e.g., 9 degrees or negative 9 degrees relative to the line L) relative to the detector positioner in order to maintain a parallel position of the surface 58 relative to the first axis A1. The direction is generally opposite that of the direction as illustrated in FIG. 13A. Again, the movements of the rotor 33, the source 13, and the detector 14 may be coordinated and/or synchronous such that the beam 15 follows and the center 56 remains substantially normal to the surface 58 of the detector 14 as the components described above move from the second position 93, 14*b* to the third position 95, 14*c*.

Further positions may be utilized of the rotor 33, source 13 and the detector 14 within the gantry 11, depending on the number of images desired for the specific application. The images captured when at any selected positions may be stitched together to form a wide field of view image, such as a wide film radiograph.

In addition to the wide field of view image, as disclosed above, the movement of the imaging system 16 may allow for a center or substantially focused image of a portion within the volume of imaging 54 that may be off the isocenter, but at the center line 56 of the beam 15. For example, with reference to FIG. 13 C, a portion of the object or area of interest or volume of interest (VOI) 57 is illustrated. The VOI 57 is not at to the isocenter C1 of the imaging system 16. Nevertheless, the VOI 57 is at the center line 56 of the beam 15. Therefore, an image or image data captured of the VOI 57 may be captured substantially at a center of the detector 14 when the detector is at the position 14*c*. Further, the central axis or line 56 of the beam 15 is substantially normal to the surface 58 of the detector 14 when the detector is at position 14*c*. Therefore, the imaging system 16 may image a portion isocenter C1 while maintaining the center line 56 of the beam substantially normal to the surface 58 of the detector 14.

In another aspect, the rotor 33 may allow a rotation which may create a stitched image utilizing a wide effective detector 17 for more than one perspective relative to the isocenter C1. Capturing of the image data to allow for generation of at least two stitched images 112, such as would be the result of multiple effective detectors as in FIG. 16 as illustrated with reference to FIGS. 17A-F below.

Figures 17A, 17B, 17C:
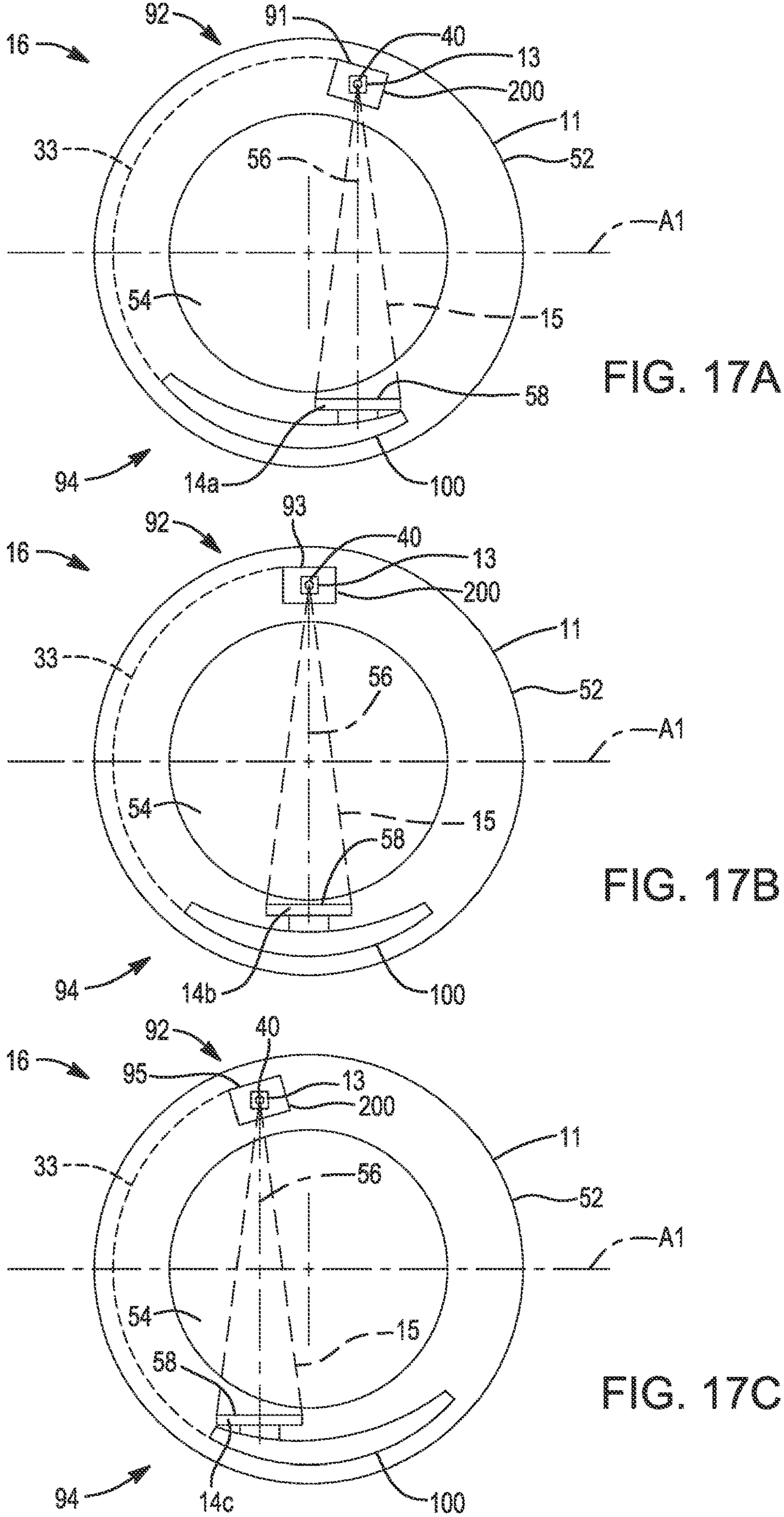
Figures 17D, 17E, 17F:
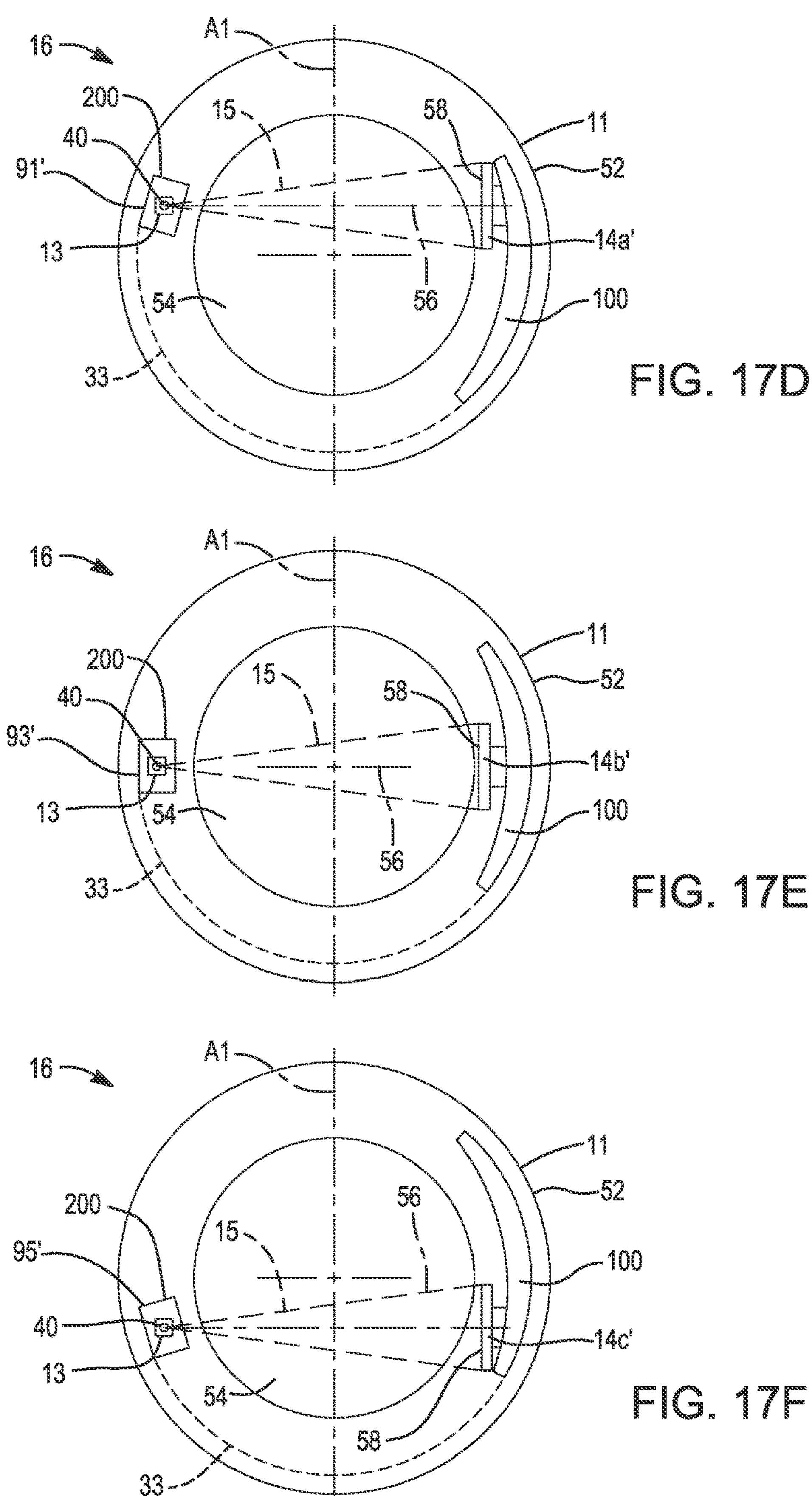

The process illustrated in FIGS. 13A-C may allow for formation of the effective detector 17, as discussed above. However, as illustrated in FIG. 16, the effective detector may be defined at any position relative to the isocenter C1 and/or the axis A1. In various embodiments, for example, the effective detector 17 may be used to generate and an anterior to posterior image of a subject, such as the subject 114. The effective detector may be formed at a different position, such as that a position 17' illustrated in FIG. 16 to allow for generation of a lateral image of the subject, such as the subject 114. The movement of the source 13 and the detector 14 may be substantially similar in either of the effective detector positions 17, 17'. Therefore, FIGS. 17A-C illustrate positions 14*a*-14*c* of the detector 14 and respective positions 91-95 of the source 13 to generate an anterior-to-posterior view. FIGS. 17D-F illustrate substantially similar or identical positions rotated 90° relative to the isocenter C1 of the imaging system 16. Therefore, the specific positions will not be repeated regarding the positions illustrated in FIGS. 17D-F other than they are illustrated augmented with a prime ('). One skilled in the art will understand that the positions may be identical to those discussed above in FIGS. 13A-C but rotated 90°, as illustrated in FIGS. 17D-F.

In various embodiments, the movement of and angle of the detector 14 and the movement of the source 13 and trajectory of the x-ray beam 15 can be coordinated and synchronized and automatically controlled by a computerized motor control system. For example, the imaging system processor 402 may recall instructions to generate a wide field of view image. The instructions may include an amount of movement and/or orientation of the rotor 33, the source 13, and the detector 14. As discussed above, at least each of these elements may move relative to one another to achieve the effective detector 17 as discussed above. Thus, based on an input, such as from the user, the processor 402 may generate signals to operate the imaging system 16 to move the various portions in the appropriate manner to achieve the wide effective detector 17.

An exemplary flow diagram showing an exemplary method 148 executed by the processor 402 for moving the rotor 33, the source 13, and the detector 14 when operating the imaging system 16 is shown in FIG. 18. The process begins at block 150, in which the imaging system 16 is prepared to begin capturing images. Block 152 includes various subblocks referring to positing the elements of the imaging system in the respective first positions as discussed above. Subblock 154 includes the rotor 33 rotating such that the x-ray source stage 200 and the source 13 are placed in the first source position 91. Subblock 156 includes rotating the source 13 such that the source 13 is angled at a first source angle. Subblock 158 includes the detector 14 translating on the detector positioner 100 to the first detector position 14*a* Subblock 160 includes positioning the detector 14 such as rotating to the first detector angle in which the surface 58 of the detector 14 is parallel to the first axis A1. Thus, block 152 may include all of the subblocks subblock 154, subblock 156, subblock 158, and subblock 160 and they may be completed simultaneously and/or in a coordinated and synchronized manner. In various embodiments, subblock 154, subblock 156, subblock 158, and subblock 160 may not be completed simultaneously.

Method 148 may proceed to block 162 after completing block 152. At block 162, the elements of the imaging system are placed in the respective second positions. Block 162 may comprise various subblocks as discussed herein. Subblock 164 includes the rotor 33 rotating such that the x-ray source stage 200 is placed in a second source position and of the source 93. Subblock 166 includes rotating the source 13 such that the source 13 is angled at a second source angle. Subblock 168 includes moving the detector 14 on the detector positioner 100 to the second detector position 14*b*. Subblock 170 includes the detector 14 positioned, such as rotated, to a second detector angle in which the surface 58 of the detector 14 is parallel to the first axis A1. Block 162, therefore, may include all of the subblock 164, subblock 166, subblock 168, and subblock 170 that may be completed simultaneously to coordinate and synchronize movements of the imaging system. In various embodiments, the subblocks 164, 166, 168, and 170 may not be completed simultaneously.

Method 148 may also proceed to further blocks, which correspond to additional imaging positions after completing block 162. For example, at block 172, the elements of the imaging system are placed in the respective nth positions. Block 172 may comprise various subblocks as discussed herein. Subblock 174 includes the rotor 33 rotating such that the x-ray source stage 200 and source 13 are placed in an nth source position. Subblock 176 includes rotating the source 13 such that the source 13 is angled at an nth source angle. Subblock 178 includes the detector 14 moving the detector on the detector positioner 100 to an nth detector position. Subblock 180 includes the detector 14 operable to be rotated to an nth detector angle in which the surface 58 of the detector 14 is parallel to the first axis A1. In block 172 the subblocks 174, 176, 178, and 180 may be completed simultaneously to achieve a coordinated and/or synchronous movement of the imaging system 16. In various embodiments, subblocks 174, 176, 178, and 180 may not be completed simultaneously.

Following block 172, method 148 may proceed to a conditional block 182, in which a determination of whether the selected imaging data for the specific application has been captured. If the selected imaging data has not been captured, the method 148 returns to block 172 for additional imaging. If the selected imaging data has been captured the method 148 may proceed to block 184, in which the method 148 ends.

Once images have been captured by the detector 14 at a selected position of the effective detector 17, additional images may be desired from another view. For example, a second view of the object may be desired which is oblique. Further, after acquiring the wide field of view, a smaller field of view image data acquisition may occur, such as of the VOI 57. Thus, the imaging system 16 may be operated to acquire the large field of view image and/or a smaller field of view. Further, the imaging system 16 may be operated to acquire a plurality of large field of view image data acquisitions with the selected coordinated and/or synchronous movements of the various portions of the imaging system 16, as discussed above.

It will also be understood that although the embodiments shown here include x-ray imaging devices having O-shaped gantries, other gantry configurations could be employed, including broken ring shaped gantries having less than full 360 degree rotational capability.

The detector arrays described herein include two-dimensional flat panel solid-state detector arrays. It will be understood, however, that various detectors and detector arrays can be used in this invention, including any detector configurations used in typical diagnostic fan-beam or cone-beam imaging systems, such as C-arm fluoroscopes. A preferred detector is a two-dimensional thin-film transistor x-ray detector using scintillator amorphous-silicon technology.

While this invention has been particularly shown and described with references to preferred embodiments thereof, it will be understood by those skilled in the art that various changes in form and details may be made therein without departing from the scope of the invention encompassed by the appended claims. For instance, although the particular embodiments shown and described herein relate in general to computed tomography (CT) x-ray imaging applications, it will further be understood that the principles of the present invention may also be extended to other medical and non-medical imaging applications, including, for example, magnetic resonance imaging (MRI), positron emission tomography (PET), single photon emission computed tomography (SPECT), ultrasound imaging, and photographic imaging.

Also, while the embodiments shown and described here relate in general to medical imaging, it will be understood that the invention may be used for numerous other applications, including industrial applications, such as testing and analysis of materials, inspection of containers, and imaging of large objects.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Instructions may be executed by a processor and may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The apparatuses and methods described in this application may be partially or fully implemented by a processor (also referred to as a processor module) that may include a special purpose computer (i.e., created by configuring a processor) and/or a general purpose computer to execute one or more particular functions embodied in computer programs. The computer programs include processor-executable instructions that are stored on at least one non-transitory, tangible computer-readable medium. The computer programs may also include or rely on stored data. The computer programs may include a basic input/output system (BIOS) that interacts with hardware of the special purpose computer, device drivers that interact with particular devices of the special purpose computer, one or more operating systems, user applications, background services and applications, etc.

The computer programs may include: (i) assembly code; (ii) object code generated from source code by a compiler; (iii) source code for execution by an interpreter; (iv) source code for compilation and execution by a just-in-time compiler, (v) descriptive text for parsing, such as HTML (hypertext markup language) or XML (extensible markup language), etc. As examples only, source code may be written in C, C++, C#, Objective-C, Haskell, Go, SQL, Lisp, Java®, ASP, Perl, Javascript®, HTML5, Ada, ASP (active server pages), Perl, Scala, Erlang, Ruby, Flash®, Visual Basic®, Lua, or Python®.

Communications may include wireless communications described in the present disclosure can be conducted in full or partial compliance with IEEE standard 802.11-2012, IEEE standard 802.16-2009, and/or IEEE standard 802.20-2008. In various implementations, IEEE 802.11-2012 may be supplemented by draft IEEE standard 802.11ac, draft IEEE standard 802.11ad, and/or draft IEEE standard 802.11ah.

A processor, processor module, module or 'controller' may be used interchangeably herein (unless specifically noted otherwise) and each may be replaced with the term 'circuit.' Any of these terms may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

Instructions may be executed by one or more processors or processor modules, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" or "processor module" as used herein may refer to any of the foregoing structure or any other physical structure suitable for implementation of the described techniques. Also, the techniques could be fully implemented in one or more circuits or logic elements.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of operating an image apparatus, comprising:
repositioning a detector to a plurality of positions to acquire image data of an object;
maintaining a surface of the detector parallel to a first axis and facing along a first line as the detector is repositioned to each position of the plurality of positions, wherein the first line is normal to the first axis, and wherein the first axis is a lateral axis extending across an imaging volume perpendicular to a central axis of a gantry; and
repositioning a beam source such that a center of a beam produced by the beam source is normal to the surface of the detector at each of the plurality of positions,
producing a large effective detector by repositioning the detector and repositioning the beam source by acquiring image data at least at a first position and a second position of the plurality of positions.

2. The method of claim 1, further comprising rotating a rotor to at least in part perform the repositioning the detector and repositioning the beam source.

3. The method of claim 1, further comprising executing instructions with a controller to control the repositioning of the detector and repositioning of the beam source, wherein the controller is configured to control the repositioning the detector and repositioning the beam source synchronously to achieve each of the plurality of positions.

4. The method of claim 1, wherein repositioning the detector includes moving the detector on rails of a detector positioner,
wherein repositioning the beam source includes swiveling the beam source.

5. The method of claim 4, further comprising rotating a rotor to at least in part perform the repositioning the detector and repositioning the beam source synchronously.

6. The method of claim 1, further comprising imaging at least a portion of the object at each position of the plurality of positions.

7. The method of claim 1, wherein the method further comprises at least one of determining a non-isocentric volume of interest using at least one image captured, determining a size of the object, determining a location and extent of truncation of at last a portion of the object in an image, and determining a region of interest and determining a field of view such that the region of interest is present in the field of view.

8. The method of claim 1, further comprising:
stitching together images acquired at each position of the plurality of positions.

9. A method of operating an image apparatus, comprising:
positioning a detector at a first position within a gantry to image a first portion of an object, wherein a surface of the detector faces a first direction in the first position and is parallel to a first axis, wherein the first axis is a lateral axis extending across an imaging volume perpendicular to a central axis of the gantry;
positioning a beam source within the gantry such that the beam source is opposed to the detector at the first position, wherein a center of a beam produced by the beam source is normal to the surface of the detector when the beam is detected by the detector at the first position;
moving the detector to a second position within the gantry to image a second portion of the object, wherein the surface of the detector faces the first direction and remains parallel to the first axis in the second position; and
moving the beam source such that the center of the beam produced by the beam source is normal to the detector when the beam produced by the beam source is detected by the detector at the second position.

10. The method of claim 9, wherein moving the beam source occurs simultaneously with moving the detector to the second position.

11. The method of claim 9, wherein moving the beam source such that the beam source comprises rotating the beam source such that the beam source faces the surface of the detector synchronously with the detector moving to the second position.

12. The method of claim 9, wherein moving the beam source such that the beam source is opposed to the detector at the second position comprises rotation of the beam source such that the beam produced by the beam source is directed to the detector.

13. The method of claim 9, wherein moving the beam source comprises moving the beam source around an interior of the gantry and synchronously rotating the beam source such that the beam produced by the beam source is directed to the detector.

14. An imaging apparatus comprising:
a source that emits a beam;
a detector located a distance from the source and configured to detect the beam;
an imaging volume between the source and the detector, a radiation beam from the source configured to pass through a portion of the imaging volume to be detected by the detector;
a detector positioner configured to reposition the detector;
a beam positioner configured to reposition the source;
a gantry housing the source, the detector, the detector positioner, and the beam positioner; and
a processor configured to execute instructions to:
direct the detector positioner to position the detector at a first position within the gantry to image a first portion of an object within the imaging volume, wherein a surface of the detector is in a first plane in the first position and the first plane is parallel to a first axis, wherein the first axis is a lateral axis extending across the imaging volume perpendicular to a central axis of the gantry;

direct the beam positioner to position the source such that the beam produced by the source is detected by the detector at the first position;

direct the detector positioner to move the detector to a second position within the gantry to image a second portion of the object within the imaging volume, wherein the surface of the detector is substantially in the first plane and remains parallel to the first axis in the second position; and direct the beam positioner to move the source such that beam is detected by the detector at the second position.

15. The imaging apparatus of claim 14, wherein the processor is configured to execute further instructions to move the source and the detector to the second position synchronously.

16. The imaging apparatus of claim 14, wherein the processor is configured to execute further instructions to control the beam positioner to rotate the source such that the beam is directed to the detector to generate image data with the beam substantially normal to the surface of the detector.

17. The imaging apparatus of claim 14, wherein the processor is configured to execute further instructions to:

generate wide field of view image based on image data acquired at the first position and the second position;

receive an input to identify a volume of interest off an isocenter within the wide field of view image; and control the detector to acquire image data of the volume of interest with the surface of the detector normal to a center of the beam.

18. The imaging apparatus of claim 14, wherein the detector positioner is configured to reposition the detector such that at least a portion of the detector extends beyond an edge of a detector positioner frame to increase an effective field of view obtainable with the detector.

19. The imaging apparatus of claim 14, wherein the detector positioner is configured to move the detector along an arcuate path defined by the positioner frame, and the detector is configured to rotate or tilt relative to the positioner frame such that the surface of the detector remains parallel to the first axis at each of a plurality of positions.

20. The imaging apparatus of claim 14, wherein the processor is configured to execute further instructions to stitch together images acquired at each of a plurality of positions of the detector to generate a wide field of view image.

* * * * *